US011814666B2

(12) United States Patent
Heijstra et al.

(10) Patent No.: US 11,814,666 B2
(45) Date of Patent: *Nov. 14, 2023

(54) GAS TESTING UNIT AND METHOD

(71) Applicant: LanzaTech NZ, Inc., Skokie, IL (US)

(72) Inventors: Bjorn Daniel Heijstra, Bergen (NL);
Sean Dennis Simpson, Evanston, IL
(US); Nicholas Bourdakos, Toronto
(CA); Jason Carl Bromley, Chicago,
IL (US); Kai-Ming Yap, Hamilton (NZ)

(73) Assignee: LanzaTech NZ, Inc., Skokie, IL (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/449,078

(22) Filed: Sep. 27, 2021

(65) Prior Publication Data

US 2022/0010350 A1    Jan. 13, 2022

Related U.S. Application Data

(63) Continuation of application No. 16/139,217, filed on Sep. 24, 2018, now Pat. No. 11,155,850, which is a
(Continued)

(51) Int. Cl.
*C12Q 1/02* (2006.01)
*G01N 30/88* (2006.01)
(Continued)

(52) U.S. Cl.
CPC ............ *C12Q 1/02* (2013.01); *C12M 21/04* (2013.01); *C12M 21/12* (2013.01); *C12M 23/44* (2013.01);
(Continued)

(58) Field of Classification Search
CPC .......... C12Q 1/02; C12P 7/065; C12M 21/04; C12M 21/12; C12M 23/44; C12M 29/18;
(Continued)

(56) References Cited

U.S. PATENT DOCUMENTS 4,263,406 A   4/1981   Bostick
7,972,824 B2  7/2011   Simpson
(Continued)

FOREIGN PATENT DOCUMENTS

CN   101918567 A   12/2010
CN   102057034 A    5/2011
(Continued)

OTHER PUBLICATIONS

Chinese Application No. 201580060371.1, Office Action and Search Report, dated Mar. 20, 2018.
(Continued)

*Primary Examiner* — Michael L Hobbs

(57) ABSTRACT

A fermentation unit and a method of carrying out fermentation are described. The fermentation unit can be transported from one facility to another to carry out a fermentation process. The fermentation unit and method allow for the fermentation of a C1-containing substrate from a source at a particular facility to produce products such as alcohols and acids. Examples of the source of the C1-containing substrate include without limitation steel manufacturing processes, coal and biomass gasification processes, coke manufacturing processes, etc. The fermentation unit can be housed within a container having a volume of less than about 6 $m^3$.

20 Claims, 4 Drawing Sheets

Related U.S. Application Data continuation of application No. 14/919,694, filed on Oct. 21, 2015, now Pat. No. 10,113,194.

(60) Provisional application No. 62/067,392, filed on Oct. 22, 2014.

(51) Int. Cl.
| | |
|---|---|
| *C12M 1/107* | (2006.01) |
| *C12M 1/00* | (2006.01) |
| *C12M 3/00* | (2006.01) |
| *C12M 1/34* | (2006.01) |
| *G01N 30/02* | (2006.01) |
| *G01N 30/46* | (2006.01) |
| *G01N 30/00* | (2006.01) |
| *C12P 7/06* | (2006.01) |
| *G01N 30/86* | (2006.01) |

(52) U.S. Cl.
CPC ............ *C12M 29/18* (2013.01); *C12M 41/00* (2013.01); *C12M 41/12* (2013.01); *C12M 41/26* (2013.01); *C12M 41/34* (2013.01); *G01N 30/02* (2013.01); *G01N 30/88* (2013.01); *C12P 7/065* (2013.01); *G01N 30/462* (2013.01); *G01N 30/8658* (2013.01); *G01N 2030/0095* (2013.01); *Y02E 50/10* (2013.01); *Y02E 50/30* (2013.01)

(58) Field of Classification Search
CPC ...... C12M 41/00; C12M 41/12; C12M 41/26; C12M 41/34; G01N 30/462; G01N 30/02; G01N 30/88; G01N 30/8658; G01N 2030/0095

See application file for complete search history.

(56) References Cited

U.S. PATENT DOCUMENTS

| | | | |
|---|---|---|---|
| 10,113,194 B2* | 10/2018 | Heijstra | ................ C12M 41/00 |
| 11,155,850 B2* | 10/2021 | Heijstra | ................ C12M 41/00 |
| 2004/0139784 A1 | 7/2004 | Srinivasan et al. | |
| 2012/0115198 A1 | 5/2012 | Gaddy | |

FOREIGN PATENT DOCUMENTS

| | | |
|---|---|---|
| CN | 103038353 A | 4/2013 |
| JP | 2002176967 A | 6/2002 |
| WO | 2010064932 A1 | 6/2010 |
| WO | 2013106403 A1 | 7/2013 |

OTHER PUBLICATIONS

International Search Report and Written Opinion, Application No. PCT/US2015/056783, dated Jan. 21, 2016, 15 pages.

Japanese Office Action for Japanese Application 2020-082012, Japanese Intellectual Property Office, dated Jun. 15, 2021.

TW Application No. 104134733, Office Action dated Apr. 20, 2021, 5 pages.

Extended European Search Report issued for European Application No. 22207775.2, dated Apr. 3, 2023, 8 pages.

* cited by examiner

GAS TESTING UNIT AND METHOD

CROSS-REFERENCE TO RELATED APPLICATION

This Application is a Continuation of U.S. application Ser. No. 16/139,217 filed on Sep. 24, 2018, now U.S. Pat. No. 11,155,850, which is a Continuation of U.S. application Ser. No. 14/919,694 filed on Oct. 21, 2015, now U.S. Pat. No. 10,113,194, which claims the benefit of U.S. Provisional Patent Application 62/067,392, filed Oct. 22, 2014, the contents of which are incorporated by reference.

FIELD OF THE INVENTION

Aspects of the invention relate to apparatuses that include separate bioreactor stages for assessing the comparative performance between a test CO-containing substrate and a reference CO-containing substrate. Advantageously, such apparatuses may be housed within a container suitable for transport (e.g., to where an industrial CO-containing waste gas is produced).

DESCRIPTION OF RELATED ART

Environmental concerns over fossil fuel greenhouse gas (GHG) emissions have led to an increasing emphasis on renewable energy sources. As a result, ethanol is rapidly becoming a major hydrogen-rich liquid transport fuel around the world. Continued growth in the global market for the fuel ethanol industry is expected for the foreseeable future, based on the increased emphasis on ethanol production in Europe, Japan, and the United States, as well as several developing nations. For example, in the United States, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. In addition, the European Union (EU) has mandated targets, for each of its member nations, for the consumption of sustainable transport fuels such as biomass-derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feedstocks is influenced by their value in the marketplace for competing uses, namely as food sources for both humans and animals. In addition, the cultivation of starch or sucrose-producing crops for ethanol production is not economically sustainable in all geographies, as this is a function of both local land values and climate. For these reasons, it is of particular interest to develop technologies that convert lower cost and/or more abundant carbon resources into fuel ethanol. In this regard, carbon monoxide (CO) is a major, energy-rich by-product of the incomplete combustion of organic materials such as coal, oil, and oil-derived products. CO-rich waste gases result from a variety of industrial processes. For example, the steel industry in Australia is reported to produce and release into the atmosphere over 500,000 metric tons of CO annually.

More recently, microorganism (bacteria) based process alternatives for producing ethanol from CO on an industrial scale have become a subject of commercial interest and investment. The ability of microorganism cultures to grow, with CO being the sole carbon source, was first discovered in 1903. This characteristic was later determined to reside in an organism's use of the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic, and acetogenic organisms have since been shown to metabolize CO. Anaerobic bacteria, such as those from the genus *Clostridium*, are known to produce ethanol from CO, $CO_2$, and $H_2$ via the acetyl CoA biochemical pathway. For example, various strains of *Clostridium ljungdahlii* that produce ethanol from gases are described in WO 00/68407; EP 1117309 A1; U.S. Pat. Nos. 5,173,429; 5,593,886; 6,368,819; WO 98/00558; and WO 02/08438. The bacterium *Clostridium autoethanogenum* sp is also known to produce ethanol from gases (Abrini et al., ARCHIVES OF MICROBIOLOGY 161: 345-351 (1994)).

Because each enzyme of an organism promotes its designated biological conversion with essentially perfect selectivity, microbial synthesis routes can achieve higher yields with lower energy costs compared to conventional catalytic routes. For example, the energy requirements for separating byproducts, which result from non-selective side reactions, from the desired products may be reduced. In addition, concerns over the poisoning of catalysts, due to impurities in the reaction medium, are diminished. Despite these apparent advantages, however, the art must address certain challenges presently associated with the microbial synthesis of ethanol from CO, particularly in terms of ensuring that the production rate is competitive with other technologies. When using CO as their carbon source, the anaerobic bacteria described above produce ethanol by fermentation, but they also produce at least one metabolite, for example, $CO_2$, methane, n-butanol, and/or acetic acid. The formation of any of these metabolites has the potential to significantly impact productivity and overall economic viability of a given process, as available carbon is lost to the metabolite(s) and the production efficiency of the desired end product is compromised. In addition, unless a metabolite (e.g., acetic acid) itself has value at the time and place of the microbial fermentation process, it may pose a waste disposal problem. Various proposals for addressing the formation of products other than the desired end product in the anaerobic fermentation of CO-containing gases to make ethanol are discussed in WO2007/117157, WO2008/115080, and WO2009/022925.

Ethanol production rate, which is a key determinant as to whether a given fermentation process is economically attractive, is highly dependent on managing the appropriate conditions for bacterial growth. For example, it is known from WO2010/093262 that the CO-containing substrate must be provided to a microbial culture at a rate that results in optimal microbial growth and/or desired metabolite production. If insufficient substrate is provided, microbial growth slows, and the fermentation product yields shift toward acetic acid at the expense of ethanol. If excessive substrate is provided, poor microbial growth and/or cell death can result. Further information regarding the relationships among operating parameters in these processes is found in WO2011/002318.

The art pertaining to biological processes for producing ethanol from CO, and particularly CO-containing waste streams such as the gaseous effluents emitted in steel production and in the chemical industry in general, is continually seeking solutions that improve overall process economics (and therefore industry competitiveness), and/or that lead to greater certainty in the adoption of relatively new technologies on an industrial scale. In this regard, the commercial performance of a given bacterial culture can be sensitive to the specific source of the CO-containing substrate, and, more particularly, the types and amounts of impurities that may reside in gaseous waste streams of a specific industrial operator (e.g., steel producer), in addition to variations in gas composition. The large investment for a commercial biological conversion process is a difficult financial commitment to undertake if the perceived risks associated with an untested, local CO-containing substrate and utilities (e.g., water source) are considered excessive. Efficient means of achieving client/investor confidence in a given technology are therefore of great importance in advancing biological conversion processes for ethanol production to a commercial reality.

SUMMARY OF THE INVENTION

The present invention is associated with the discovery of apparatuses and associated methods for the efficient evaluation of C1-containing substrates, and especially for such evaluation that is conducted locally, or on-site, at a prospective facility for implementation of a biological conversion process for ethanol production from a C1 carbon source. Typically, the C1-containing substrate comprises at least one C1 carbon source selected from the group consisting of CO, $CO_2$, and $CH_4$. Importantly, it has been determined that the precise composition of a given, industrial C1-containing substrate is often difficult to reproduce at a remote facility (e.g., a laboratory or a pilot-scale or demonstration-scale process), at least to the extent required for the accurate prediction of commercial performance. Importantly, without sufficient confidence that a given process can achieve its performance objectives, large capital expenditures needed for scale-up (e.g., process design and engineering) cannot be justified. In this regard, even trace amounts of certain contaminants (e.g., hydrocarbons or heteroatom-containing hydrocarbons) can adversely affect a bacterial culture, which is a liquid-based system that is prone to extract such heavier molecules from the C1-containing substrate, allowing such molecules to accumulate in internal and external liquid recycle loops of a bioreactor. Moreover, fluctuations in the local gas composition are similarly difficult to reproduce in an off-site testing facility, and in many cases, the extent of such fluctuations cannot be known or appreciated without direct, local access to the C1-containing substrate. Furthermore, the suitability of other aspects that may be significant to the locality of a prospective, commercial biological conversion facility (e.g., a local water source to be used in the bacterial culture medium) should be further evaluated and confirmed, prior to significant investment decisions.

Advantageously, apparatuses and methods described herein can be used to identify and remediate causes of sub-optimal performance (e.g., metabolite productivity and/or substrate utilization). The degree to which pretreatment of the C1-containing substrate and/or other locally sourced additives to the process must be implemented, or enhanced, can advantageously be determined in advance of commercial-scale operation, improving the accuracy of the commercial design and associated cost estimates. Furthermore, an on-site demonstration of efficacy provides an important degree of reassurance to both the provider and user alike, of a prospective biological conversion process, operating with the local (i.e., the actual or industrial) supply of C1-containing substrate and possibly other local additives.

Particular embodiments of the invention are directed to gas testing units comprising two bioreactor stages, and in many cases using only two bioreactor stages, with sufficient instrumentation, process equipment, and analytical capability for comparatively evaluating a test C1-containing substrate, and, importantly, with sufficient size constraints to allow transportability.

In one aspect, the present disclosure provides a gas testing unit, comprising: (a) a first bioreactor stage for evaluating the performance of a reference C1-containing substrate; (b) a second bioreactor stage for evaluating the performance of a test C1-containing substrate; and (c) an analytical section configured for analysis of both gaseous and liquid products of the first and second bioreactors; wherein the gas testing unit is capable of being housed within a container having a volume of less than about 6 $m^3$ and transportable to multiple locations.

The gas testing unit is capable of being housed within a box having length, width, and height dimensions of less than about 1.8 meters each, or less than about 1.6 meters each, or less than 1.3 meters each. In certain embodiments, the box has one of the length, width, and height dimensions of less than about 1.6 meters, and the other two of the length, width, and height dimensions of less than about 1.3 meters.

The analytical section of the gas testing system comprises a gas chromatography (GC) analyzer having first and second chromatography columns configured, respectively, for analysis of the gaseous and the liquid products.

The bioreactors of the first and second bioreactor stages each comprise a circulated loop bioreactor. The first and second bioreactor stages each further comprise external recycle loops and recirculation pumps for recycling liquid withdrawn proximate bottom ends of the bioreactors to proximate, opposite top ends of the bioreactors.

The gas testing unit may further comprise an operating control system for controlling one or more operating parameters selected from the group consisting of fresh culture medium addition rate, gaseous C1-containing substrate feed rate, reactor temperature, and reactor pH. In certain embodiments, the one or more operating parameters include reactor pH, and the control system includes instrumentation for controlling the flow of a basic neutralizing agent to the bioreactor, based on a measured reactor pH.

In certain embodiments, the gas testing unit comprises a safety control system for suspending the flow of at least the test C1-containing substrate or the reference C1-containing substrate, in response to a measurement of an ambient C1 concentration at above a threshold concentration.

In a second aspect, the present disclosure provides a method for evaluating suitability of a test C1-containing substrate for use in a biological conversion process, the method comprising (a) feeding a reference C1-containing substrate to a first bioreactor containing a first culture of a C1-fixing microorganism; (b) feeding the test C1-containing substrate to a second bioreactor containing a second culture of the C1-fixing microorganism; and (c) analyzing both gaseous and liquid products of the first and second bioreactors to determine the performance of the first and second bioreactors; wherein the suitability of the test C1-containing substrate is established from a comparison of the performance of the first bioreactor, relative to the performance of the second bioreactor. In certain embodiments, at least a portion of step (a) and step (b) are carried out simultaneously.

In certain embodiments, the C1-fixing microorganism is a carboxydotrophic microorganism from the genus *Clostridium*. Preferably, the C1-fixing microorganism is selected from the group consisting of *Clostridium autoethanogenum*, *Clostridium ljungdahlii*, and *Clostridium ragsdalei*.

In certain embodiment, the method comprises feeding the reference C1-containing substrate to the second bioreactor, prior to feeding the test C1-containing substrate to the second bioreactor in step (b).

The test C1-containing substrate is an industrial C1-containing waste gas stream that has been pretreated to remove a contaminant. In certain embodiments, the test C1-containing substrate is a raw industrial gas stream. In certain embodiments, the method comprises testing a raw C1-containing substrate to determine the biological process is feasible on an untreated waste gas stream.

In one embodiment, the analyzing step (c) comprises measuring concentrations of C1 in the gaseous products of the first and second bioreactors and measuring concentrations of ethanol and at least one further metabolite in the liquid products of the first and second bioreactors. Additionally, in accordance with the invention at least one of the first and second cultures of a C1-fixing microorganism may comprise a culture medium prepared with, or supplemented with, a local water source. In some embodiments, the performances of the first and second cultures are assessed simultaneously over a test period of at least about 7 days In a further aspect, the present disclosure provides a method for determining whether a test C1-containing substrate supports a biological conversion process. The method comprises: (a) maintaining separate, first and second cultures of a C1-fixing microorganism, utilizing a reference C1-containing substrate as a nutrient for producing ethanol and at least one further metabolite; (b) changing from the reference C1-containing substrate, as the nutrient to the second culture, to a test C1-containing substrate; (c) assessing the performance of the first culture, relative to that of the second culture, under a same set of target operating conditions, but using the different, reference and test C1-containing substrates; (d) in the event of not obtaining a minimum performance deficit of the second culture in step (c), confirming that the test C1-containing substrate supports the biological conversion process; (e) in the event of obtaining the minimum performance deficit in step (c), pretreating or enhancing pretreatment of the test C1-containing substrate to provide a higher quality test C1-containing substrate, relative to the test C1-containing substrate used to assess performance in step (c).

In one embodiment, the method further comprises (f) assessing the performance of the first culture, relative to that of a third culture, under the same set of target operating conditions, but using the different, reference and higher quality test C1-containing substrates; and (g) in the event of not obtaining the minimum performance deficit of the third culture in step (f), confirming that the higher quality test C1-containing substrate supports a biological conversion process.

In certain embodiments, different water sources are used to prepare the first and second cultures or supplement the first and second cultures.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which similar features are identified by similar reference numbers (e.g., bioreactor 100 of FIG. 1A and bioreactors 100a, 100b of FIG. 2).

FIGS. 1-3 should be understood to present an illustration of the disclosure and/or principles involved. In order to facilitate explanation and understanding, simplified equipment and process flows are depicted in FIGS. 1 and 2, and the relative dimensions of different equipment are not necessarily drawn to scale. Details including some valves, instrumentation, and other equipment and systems not essential to the understanding of the disclosure are not shown. As is readily apparent to one of skill in the art having knowledge of the present disclosure, apparatuses, and methods for testing whether a given C1-containing substrate and/or local additives support a biological conversion process will have configurations and components determined, in part, by their specific use.

DETAILED DESCRIPTION

Figure 1A:
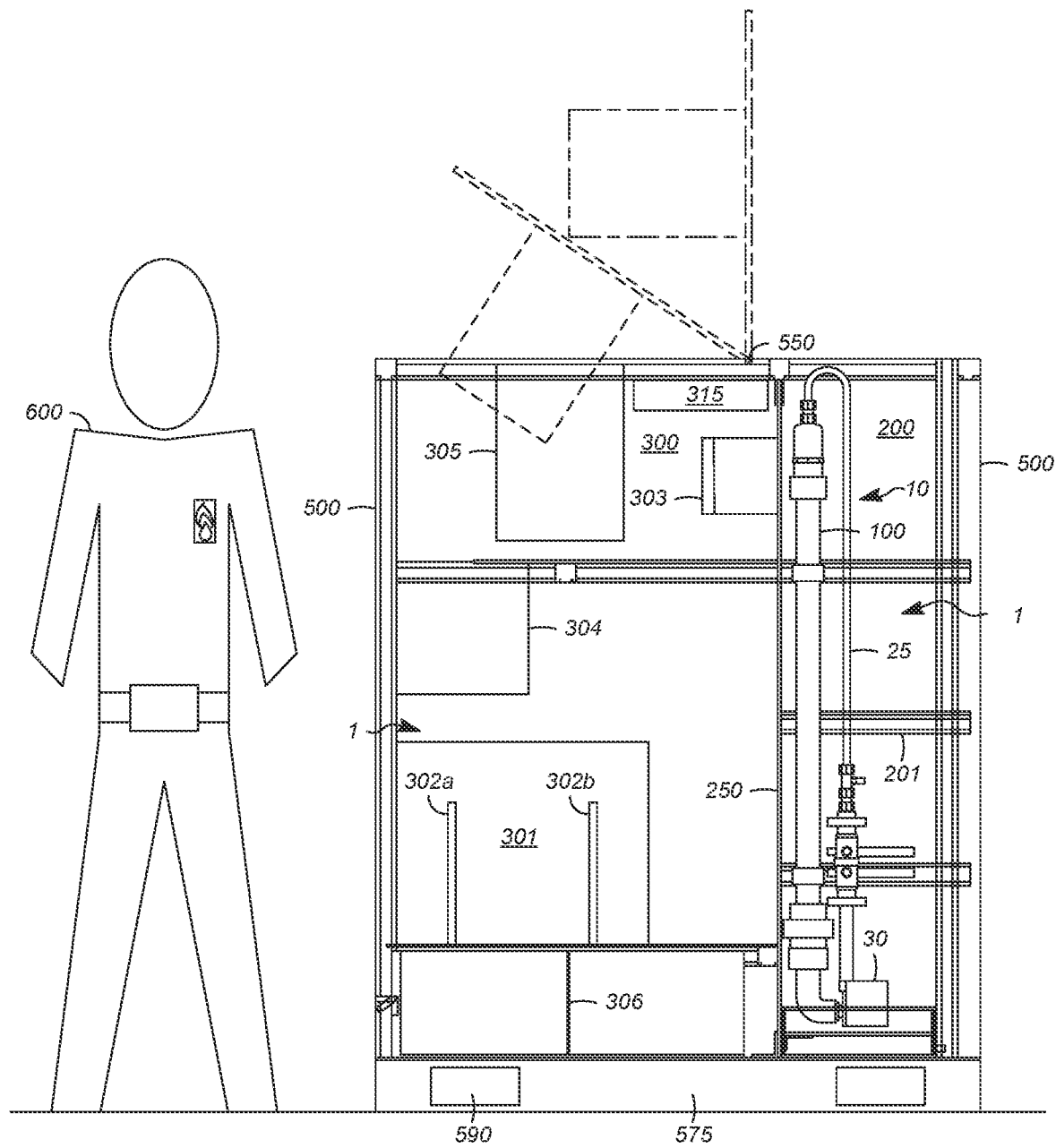
FIGS. 1A and 1B depict sectional side and rear views, respectively, of representative, transportable gas testing units as described herein.

The invention is associated with the important recognition that a test (or local) C1-containing substrate can be effectively evaluated, for the purposes identified above, using only a selected portion of the equipment otherwise used for implementing a biological C1 conversion process with maximum productivity and yield of a desired product. The C1 containing substrate typically comprises at least one C1 carbon source selected from the group consisting of CO, $CO_2$, and $CH_4$. For example, the C1 containing substrate may be a gaseous substrate containing CO. The C1 containing substrate may also comprise $H_2$ and/or $N_2$. For example, a parallel bioreactor stage system, with separate, first and second bioreactors for comparative testing of a test gas and a reference gas, can provide the necessary information to confirm that the locally available gas feed and/or additives support a commercial process, even without reaching commercial levels of performance (e.g., in terms of liquid product ethanol titers). Only a subset of the actual bioreactor components, process vessels, instrumentation, and analyzers are required, making it possible for representative gas testing units to be housed and transported (e.g., in the cargo bay of a 747 jetliner) to the prospective facility. Particular efficiencies may be gained, for example, by having only two bioreactors for evaluating test and reference gases, respectively, with no reactor internal distribution devices, except optionally liquid distribution devices (e.g., shower heads) for feeding liquid to the tops of the bioreactors from external recycle loops. Other efficiencies may be gained from using gas chromatography (GC) for analysis of both gaseous and liquid products. Yet further efficiencies may be gained by avoiding, at each bioreactor stage, the separation and recycling of a C1-fixing microorganism. By exploiting these and other efficiencies, gas testing units may advantageously be made transportable (e.g., by air, sea, or land) to a remote site of a prospective, commercial-scale installation of a biological conversion process for producing ethanol from a C1-containing substrate. The gas testing units include sufficient equipment for on-site evaluation of the locally available C1-containing substrate and process additives such as water but without all of the requirements of (i) reactor systems needed for productivity maximization, and/or (ii) analytical systems and instrumentation for comprehensive monitoring and control of all process variables. Such requirements are generally not aligned with the objective of transportability. Advantageously, it has been determined that qualitative results (e.g., in comparison with a reference test), as opposed to quantitative results, can provide a meaningful evaluation for gas quality validation purposes and/or identify areas in which a remedial measure is necessary to address a performance deficit.

The present invention relates to gas testing units that operate by, and associated methods that otherwise involve, the production of a desired end product, such as ethanol, from the biological conversion of a C1 carbon source in a gaseous C1-containing substrate. First and second bioreactor stages of the gas testing units can be fed, for example, with a reference (or control) C1-containing substrate and a test (or industrially available) C1-containing substrate for parallel or simultaneous performance evaluation, in order to establish a comparison that provides useful information in terms of establishing that a specific, test C1-containing substrate is suitable for a given process. Each of the bioreactor stages comprises a bioreactor that, in operation, includes a liquid culture medium containing a C1 fixing microorganism (bacterial culture). In addition to the desired end product, the biological conversion processes, occurring in each of the bioreactor stages, additionally generate undesired or less desired metabolites, which, like the desired product (e.g., ethanol), can be detected in liquid products withdrawn from these stages. Examples of such metabolites are acetate (e.g., in the form of acetic acid) and 2,3-butanediol. The terms "acetate" or "acetic acid" refer to the total acetate present in the culture medium, either in its anionic (dissociated) form (i.e., as acetate ion or $CH_3COO^-$) or in the form of free, molecular acetic acid ($CH_3COOH$), with the ratio these forms being dependent upon the pH of the system. As described below, a basic neutralizing agent such as aqueous ammonium hydroxide ($NH_4OH$) or aqueous sodium hydroxide (NaOH) may be used to control the pH of the culture medium in a given bioreactor (e.g., to a pH setpoint value that may be any specific pH value between pH=4.5 and pH=8.0), by neutralizing the formed acetic acid. Representative pH ranges at which bioreactors are maintained (or controlled) for carrying out the processes described herein are generally any pH value (set point) within the range from about 4.0 to about 8.0, such as from about 5.0 to about 6.5 (e.g., pH=5.0, 5.5, or 6.0).

Representative C1-fixing bacterium are those from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

A "microorganism" is a microscopic organism, especially a bacterium, archea, virus, or fungus. The microorganism of the invention is typically a bacterium. As used herein, recitation of "microorganism" should be taken to encompass "bacterium."

The microorganism of the invention may be further classified based on functional characteristics. For example, the microorganism of the invention may be or may be derived from a C1-fixing bacterium, an anaerobe, an acetogen, an ethanologen, a carboxydotroph, and/or a methanotroph. Table 1 provides a representative list of microorganisms and identifies their functional characteristics.

TABLE 1

| | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/−[1] | − | +/−[2] | − |
| *Alkalibaculum bacchii* | + | + | + | + | + | + | − |
| *Blautia product* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[3] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | −[4] | + | + | − |
| *Oxobacter pfennigii* | + | + | + | − | + | + | − |
| *Sporomusa ovata* | + | + | + | − | + | +/−[5] | − |
| *Sporomusa silvacetica* | + | + | + | − | + | +/−[6] | − |
| *Sporomusa sphaeroides* | + | + | + | − | + | +/−[7] | − |
| *Thermoanaerobacter kivui* | + | + | + | − | + | − | − |

[1] *Acetobacterium woodii* can produce ethanol from fructose, but not from gas.
[2] It has been reported that *Acetobacterium woodii* can grow on CO, but the methodology is questionable.
[3] It has not been investigated whether *Clostridium magnum* can grow on CO.
[4] One strain of *Moorella thermoacetica*, *Moorella* sp. HUC22-1 has been reported to produce ethanol from gas.
[5] It has not been investigated whether *Sporomusa ovata* can grow on CO.
[6] It has not been investigated whether *Sporomusa silvacetica* can grow on CO.
[7] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for the synthesis of acetyl-CoA and acetyl-CoA-derived products, such as acetate (Ragsdale, Biochim Biophys Acta, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, NY, 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, Arch Microbiol, 161: 345-351, 1994 (*Clostridium autoethanogenum*), Tanner, Int J System Bacteriol, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, Biotechnol Bioeng, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins have been found to be the same in all species (Kopke, Curr Opin Biotechnol, 22: 320-325, 2011).

Thus, in summary, many of the characteristics of *Clostridium autoethanogenum*, *Clostridium ljungdahlii*, or *Clostridium ragsdalei* are not specific to that species but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, Arch Microbiol, 161: 345-351, 1994), LBS1560 (DSM19630) (WO 2009/064200), and LZ1561 (DSM23693). Isolates and mutants of *Clostridium ljungdahlii* include ATCC 49587 (Tanner, Int J Syst Bacteriol, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol. In certain embodiments, microbial biomass itself may be considered a product.

Generally, the same microorganisms are used in the first and second bioreactors; however, it is also possible in some embodiments to use different C1-fixing microorganisms in the different bioreactors.

Representative C1 containing substrates and particularly the test C1 containing substrates as described herein include broadly any C1-carbon source. A C1-carbon source refers a one carbon-molecule that serves as a partial or sole carbon source for the microorganism of the invention. For example, a C1-carbon source may comprise one or more of CO, $CO_2$, or $CH_4$. Preferably, the C1-carbon source comprises one or both of CO and $CO_2$. The substrate may further comprise other non-carbon components, such as $H_2$, $N_2$, or electrons. The C1 containing substrate may contain a significant proportion of CO, preferably at least about 5% to about 99.5% CO by volume. Such substrates are often produced as waste products of industrial processes such as steel manufacturing processes or non-ferrous product manufacturing process. Other processes in which gaseous CO-containing substrates are generated include petroleum refining processes, biofuel production processes (e.g., pyrolysis processes and fatty acid/triglyceride hydroconversion processes), coal and biomass gasification processes, electric power production processes, carbon black production processes, ammonia production processes, methanol production processes, and coke manufacturing processes. A number of chemical industry effluents, as well as syngases (containing both CO and $H_2$) produced from a variety of substrates, can likewise serve as potential CO-containing substrates. Specific examples include effluents from the production of phosphate and chromate. Advantageously, wastes (e.g., waste gases) from these processes may be used as described herein for the beneficial production of useful end products such as ethanol. The substrate and/or C1-carbon source may be or may be derived from a waste or off-gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be or may be derived from syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

In connection with substrates and/or C1-carbon sources, the term "derived from" refers to a substrate and/or C1-carbon source that is somehow modified or blended. For example, the substrate and/or C1-carbon source may be treated to add or remove certain components or may be blended with streams of other substrates and/or C1-carbon sources.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

It has been determined that the precise composition of a given, industrial C1-containing substrate is often difficult to reproduce at a remote facility (e.g., a laboratory or a pilot-scale or demonstration-scale process), at least to the extent required for the accurate prediction of commercial performance. Importantly, without sufficient confidence that a given process can achieve its performance objectives, large capital expenditures needed for scale-up (e.g., process design and engineering) cannot be justified. In this regard, even trace amounts of certain contaminants (e.g., hydrocarbons or heteroatom-containing hydrocarbons) can adversely affect a bacterial culture, which is a liquid-based system that is prone to extract such heavier molecules from the C1-containing substrate, allowing such molecules to accumulate in internal and external liquid recycle loops of a bioreactor. Moreover, fluctuations in the local gas composition are similarly difficult to reproduce in an off-site testing facility, and in many cases, the extent of such fluctuations cannot be known or appreciated without direct, local access to the C1-containing substrate. Furthermore, the suitability of other aspects that may be significant to the locality of a prospective, commercial biological conversion facility (e.g., a local water source to be used in the bacterial culture medium) should be further evaluated and confirmed, prior to significant investment decisions.

The use of industrial C1 containing substrates in a biological conversion process has been shown to present numerous challenges. The presence of substances other than the primary gas components (such as CO, $H_2$, $N_2$, $CO_2$) that may have a detrimental impact on the fermentation process. Furthermore, the flow rate of the gas from an industrial process is dependent on the operating parameters of that process and is not tailored to provide a consistent volumetric gas feed rate (e.g. in $Nm^3/hr.$) to a downstream fermentation process. The chemistry of the gas in terms of the relative amounts of each of the constituents (both primary components and contaminants) change, often rapidly, with time according to the operating parameters and inputs to the upstream industrial process.

Perhaps the most significant challenge to the use of industrial off gas as the sole carbon and energy feedstock to a gas fermentation process for product synthesis is the presence of a broad spectrum of bactericidal or toxic contaminants. The negative impact of contaminants from industrially produced syngas product of gasified biomass on microbial fermentation has been well documented. These gases contain both tars and nitrogen compounds that have been consistently demonstrated to inhibit microbial growth and productivity, particularly among carboxydotrophic organisms using CO and $H_2$ as their sole source of carbon and energy (Ahmed et al. 2006). Nitric oxide found in syngas has been shown in several studied to be inhibitory to carboxydotrophic organisms such as *C. carboxydivorans* and *C. ragsdalei* at concentrations as low as 40 ppm (Datar et. al. 2004; Lewis et. al. 2006; Ahmed and Lewis, 2007; Kundiyana et. al. 2010. Other studies demonstrated that tars composed of benzene, toluene ethylbenzene and p-xylene (all compounds found in off-gases from steel making described in table 2) were also found to be inhibitory to the productivity and viability of carboxydotrophic organisms (Ahmed et. al 2006; Lewis et. al. 2006).

For example, off-gases produced as an inevitable consequence of the steel making process contain CO and, in some cases, $H_2$, and epitomize the challenge associated with using industrial off gases as described above. Typically, waste gases from steel manufacturing processes contain little or no hydrogen. Further, the multiple contaminating compounds found in these off-gases are well known and have been documented (see table 2). The number and variety of contaminants found in a steel off-gas stream are certainly much greater than that reported to be present in other industrial gases such as biomass-derived syngas. This increase in both the number and variety of contaminants presents a more significant challenge to a fermentation system. Although the "additive" effect of contaminants on the biological processes difficult to predict exactly, it is anticipated that the detrimental effect will be much more severe. Amongst the 15 most abundant contaminants passing into the vent or stacks as part of the off-gas from the steelmaking process are compounds such as oxides of nitrogen, sulfur dioxide, benzene, toluene, cyanide and fluoride compounds each of which are understood to be toxic to bacteria.

As mentioned above, tars composed of benzene, toluene, ethylbenzene, and p-xylene have been found to have a highly detrimental effect on the viability and productivity of *C. carboxydivorans* (Lewis et. al. 2006). The relative toxicity of benzene, toluene, and xylene to anaerobic bacteria was described by Payne and Smith (1983). However, as noted above, this and other compounds are present in steel mill gas together with a variety of other potentially toxic compounds. The additive impact of heavy metals such as cadmium, nickel, and zinc on the toxicity of toluene was described by (Amor et. al. 2001). These data clearly demonstrate that microbial performance in the presence of toluene is significantly and detrimentally impacted by the addition of these heavy metals individually. In steel mill off-gas, these metals are present together, which one would expect would provide an even greater challenge to microbial performance and productivity.

Significantly, it is difficult to provide a test stream in a laboratory setting that is adequately representative of an industrial gas stream. Importantly, even in gas streams from similar industries, the types and number of contaminants present in the individual gas stream will vary significantly. Even within a single plant or facility, the composition of the exhaust gas may vary depending on upstream conditions and the sourced raw material provided to the industrial process. Furthermore, compressing gases typically changes the gas composition. In particular, at high pressure, contaminant tend to drop out of the gaseous phase. This causes a discrepancy/variation between the exit gas at the site, and the test sample provided to a laboratory.

Table 2 shows all air emissions (Point source+Fugitive1) in Kilograms from the BlueScope Steel Port Kembla Steelworks—Port Kembla, NSW, Australia as reported in the National Pollution Inventory (NPI)(http://www.npi.gov.au). This emissions data shows the typical pollution causing components of off-gases from the BlueScope Steel Port Kembla Steelworks-Port Kembla, NSW, Australia.

TABLE 2

| Substance | Air Total (kg) |
| --- | --- |
| Oxides of Nitrogen | 7927779 |
| Sulfur dioxide | 7498915 |
| Particulate Matter 10.0 um | 1722175 |
| Ammonia (total) | 735551 |
| Sulfuric acid | 259163 |
| Total Volatile Organic Compounds | 240305 |
| Hydrochloric acid | 190953 |
| Benzene | 130905 |
| Particulate Matter 2.5 um | 110063 |
| Hydrogen sulfide | 81748 |
| Toluene (methylbenzene) | 20220 |
| Cyanide (inorganic) compounds | 19483 |
| Fluoride compounds | 16780 |
| Methanol | 12131 |
| Methyl isobutyl ketone | 10775 |
| Zinc and compounds | 8228 |
| Manganese & compounds | 4001 |
| Chlorine & compounds | 3221 |
| Xylenes (individual or mixed isomers) | 2583 |
| Lead & compounds | 2391 |
| n-Hexane | 1142 |
| Styrene (ethenylbenzene) | 900 |
| Copper & compounds | 575 |
| Cadmium & compounds | 425 |
| Nickel & compounds | 323 |

TABLE 2-continued

| Substance | Air Total (kg) |
|---|---|
| Boron & compounds | 247 |
| Polycyclic aromatic hydrocarbons (B[a]Peq) | 192 |
| Chromium (III) compounds | 176 |
| Mercury & compounds | 168 |
| Ethanol | 123 |
| 1,3-Butadiene (vinyl ethylene) | 120 |
| Phenol | 115 |
| Selenium & compounds | 112 |
| Chromium (VI) compounds | 69 |
| Biphenyl (1,1-biphenyl) | 60 |
| Arsenic & compounds | 47 |
| Formaldehyde (methyl aldehyde) | 47 |
| Acetone | 26 |
| Antimony & compounds | 18 |
| Ethylbenzene | 18 |
| Carbon disulfide | 13 |
| Cobalt & compounds | 8 |
| Beryllium & compounds | 2 |
| Nitric acid | 1 |
| Polychlorinated dioxins and furans (TEQ) | 1.35E−04 |

[1]Point source emissions flow into a vent or stack and are emitted through a single point source into the atmosphere. Examples are the exhaust system of a boiler or stationary combustion engine powered equipment.
Fugitive emissions are emissions that are not released via a vent or stack. Examples of fugitive emissions include exhaust emissions from vehicles, evaporative emissions from vehicle fuel tanks, volatilization of vapor from vats or fuel and other volatile organic liquid storage tanks, open vessels, spills, and materials handling. Emissions from ridgeline roof vents, louvers and open doors of a building, equipment leaks, valve leaks, and flanges are other types of fugitive emissions.

As described below, a specific type of bioreactor that is particularly useful in the gas testing units and methods described herein is a circulated loop reactor in which the gaseous C1-containing substrate is typically distributed (e.g., sparged) into the bottom of a riser section, at or near the lower end of the reactor containing the bacterial culture medium in a continuous liquid phase. Rising gas bubbles are confined to the riser section during their upward movement through the continuous liquid phase until any unconsumed and undissolved gas is released into a continuous gas phase (i.e., vapor space or headspace) above the liquid level and extending to the upper end of the reactor. Circulation of the continuous liquid phase in the riser section may be induced by the relatively low density, central portion, through which the majority of the rising gas bubbles pass, in combination with the relatively high density, peripheral (outer) portion, having little or no gas holdup. Internal liquid circulation can, therefore, be established through net upward movement of the liquid in the central portion and net downward movement in the peripheral portion. As described in greater detail below, a bioreactor stage, comprising a circulated loop reactor, may also include forced liquid circulation external to the reactor, preferably through the withdrawal of liquid from the bottom end of the reactor and introduction of the withdrawn liquid into the top end of the reactor, thereby providing countercurrent gas-liquid flow in the reactor headspace.

The term "bioreactor," as well as any bioreactor that may be included as part of a "bioreactor stage," of a gas testing unit is not limited to a circulated loop reactor, but more broadly includes any suitable vessel, or section within a vessel, for maintaining a liquid volume of culture medium with a C1-fixing microorganism that may be used to carry out the biological processes described herein, which may also be referred to as fermentation processes to the extent that they are generally conducted anaerobically. Particular types of bioreactors can include any vessels suitable for two-phase (gas-liquid) contacting, for example, counter-current flow reactors (e.g., with an upwardly-flowing vapor phase and downwardly-flowing liquid phase) or co-current flow reactors (e.g., with upwardly-flowing gas and liquid phases). In such two-phase contacting vessels, it is possible for the liquid phase to be the continuous phase, as in the case of gas bubbles flowing through a moving column of liquid. Otherwise, it is possible for the vapor phase to be the continuous phase, as in the case of a dispersed liquid (e.g., in the form of droplets) flowing through a vapor space. As in the case of a circulated loop reactor, different zones of a bioreactor may be used to contain a continuous liquid phase and a continuous gas phase.

Specific examples of bioreactors include Continuous Stirred Tank Reactors (CSTRs), Immobilized Cell Reactors (ICRs), Trickle Bed Reactors (TBRs), Moving Bed Biofilm Reactor (MBBRs), Bubble Columns, Gas Lift Fermenters, and Membrane Reactors such as Hollow Fiber Membrane Bioreactors (HFMBRs). Suitable bioreactors may include static mixers, or other vessels and/or devices (e.g., towers or piping arrangements), configured for contacting the gaseous CO-containing substrate with the liquid bacterial culture medium (e.g., with dissolution and mass transport kinetics favorable for carrying out the biological conversion). The phrases "plurality of bioreactors" or bioreactors that may be included in a "plurality of bioreactor stages" are meant to include bioreactors of more than a single type, although in some cases the plurality of bioreactors may be of one type (e.g., circulated loop reactors).

Some suitable process streams, operating parameters, and equipment for use in the biological processes described herein are described in U.S. patent application Publication No. US2011/0212433, which is hereby incorporated by reference in its entirety.

Certain embodiments relate to gas testing units, comprising a first bioreactor stage for evaluating the performance of a test C1-containing substrate and a second bioreactor stage for evaluating the performance of a reference C1-containing substrate. An analytical section is configured for analysis of both gaseous and liquid products of the first and second bioreactors. The gas testing unit is housed, or at least capable of being housed, within a container generally having a volume of less than about 6 $m^3$ (e.g., from about 0.5 $m^3$ to about 6 $m^3$), typically less than about 3 $m^3$ (e.g., from about 1 $m^3$ to about 3 $m^3$), and often less than about 2.5 $m^3$ (e.g., from about 1.5 $m^3$ to about 2.5 $m^3$). In view of such size constraints, the gas testing unit is transportable to multiple locations, e.g., for evaluating a test (or local) C1-containing substrate and optionally other local additives, such as a local water source. According to further representative embodiments, the gas testing unit is housed, or at least capable of being housed, within a box or other container having length, width, and height dimensions of less than about 1.8 meters each (e.g., each of these dimensions being within a range from about 1.0 meters to about 1.8 meters), or less than about 1.6 meters each (e.g., each of these dimensions being within a range from about 1.0 meters to about 1.6 meters). Such a box or other container may have one of its length, width, and height dimensions being less than about 1.6 meters (e.g., within a range from about 1.0 meters to about 1.6 meters), and the other two of these dimensions being less than about 1.3 meters (e.g., within a range from about 0.8 meters to about 1.6 meters).

Other embodiments relate to methods for evaluating the suitability of a test C1-containing substrate for use in a bioconversion process. The methods comprise (a) feeding a reference C1-containing substrate to a first (reference) bioreactor containing a first culture of a C1-fixing microorganism and (b) feeding the test C1-containing substrate to a second (test) bioreactor containing a second culture of a C1-fixing microorganism. The methods further comprise (c) analyzing both gaseous and liquid products of the first and second bioreactors to determine the performance of the first and second bioreactors. The suitability of the test C1-containing substrate is established from a comparison of the performance of the first bioreactor, relative to the performance of the second bioreactor. Preferably, at least a portion of the steps (a) and (b) above are carried out simultaneously (i.e., at least a portion of these steps overlap in time). Typically, steps (a) and (b) are carried out simultaneously (or at least substantially simultaneously), for a simultaneous operating period, or test period, of several days (e.g., at least about 3 days, such as from about 3 to about 21 days; at least about 5 days, such as from about 5 days to about 21 days; or at least about 7 days, such as from about 7 days to about 14 days), in order to assess the performances of the microorganism cultures in carrying out the biological conversion process. According to one embodiment, for example, the entirety of the duration of step (b), in which the test C1-containing substrate is fed to the second bioreactor, may be encompassed by the duration of step (a), in which the reference C1-containing substrate is fed to the first bioreactor. This will occur, for example, in the case of commencing the operation of both the first and second bioreactors using the reference C1-containing substrate, followed by changing the feed to the second bioreactor from the reference C1-containing substrate to the test C1-containing substrate. In representative embodiments, therefore, the methods may further comprise feeding the reference C1-containing substrate to the second bioreactor, prior to step (b).

In addition to evaluating test C1-containing substrates, representative methods may alternatively, or in combination, evaluate local additives, such as a local water source, using the apparatuses and methods described herein, by determining or assessing comparative performance. In the case of evaluating water quality, for example, different water sources may be used to prepare and/or supplement (e.g., with fresh culture medium) the first and second bacterial cultures. According to one embodiment, local conditions may be evaluated by using a local water source (e.g., local process water or local potable water) to prepare and supplement (e.g., in the fresh culture medium added) the bacterial culture of the second bioreactor, in combination with feeding the test C1-containing substrate to this culture. In another embodiment, the same local water source may be used to prepare and supplement the bacterial cultures of both bioreactors, such that the test C1-containing substrate itself can be evaluated against a baseline using the same water source. In yet other embodiments, the same C1-containing substrate (e.g., either the reference or the test C1-containing substrate) may be fed to both bioreactors, in order to evaluate the effect of different water sources alone (e.g., a local process water source or a local potable water source, compared to a purified water source such as distilled water).

Yet other embodiments relate to methods for determining whether a test C1-containing substrate supports a biological conversion process. Representative methods comprise (a) maintaining separate, first and second cultures of a C1-fixing microorganism, each utilizing a reference C1-containing substrate as a nutrient for producing ethanol and at least one further metabolite and (b) changing from the reference C1-containing substrate, as the nutrient to the second culture, to a test C1-containing substrate. The methods further comprise (c) assessing the performance of the first culture, relative to that of the second culture, under the same target operating conditions (e.g., operating set points of automatically and/or manually controlled operating parameters, for example bioreactor pH in some cases), but using the different, reference and test CO-containing substrates. The methods further comprise (d) in the event of not obtaining a minimum performance deficit (or offset) of the second culture in step (c), confirming that the test C1-containing substrate supports the biological conversion process. The methods may additionally comprise (e) in the event of obtaining the minimum performance deficit, or a greater performance deficit, in step (c), pretreating, or enhancing the existing pretreatment, of the test C1-containing substrate to provide a higher quality test C1-containing substrate, relative to the test C1-containing substrate used to assess performance in step (c).

According to alternative embodiments, step (e) in the above methods may comprise a remedial measure other than improving the quality of the test C1-containing substrate by pretreating or enhancing the existing pretreatment. Such a remedial measure may, for example, include improving the quality of a local additive, such as a local water source, or otherwise substituting a higher quality additive, for example, local potable water for local process water. Other remedial measures may include adjustments of operating conditions, such as bioreactor temperature, pressure, and/or pH. Any type of remedial measure may be accompanied by re-inoculation of the second bioreactor with a bacterial culture (e.g., a third culture), followed by assessing the performance of the first culture (or other culture utilizing the reference C1-containing substrate as a nutrient, or other reference condition) relative to that of the re-inoculated culture for testing the remedial measure (e.g., under the same set of target operating conditions, but using the different, reference and higher quality test C1-containing substrates, and/or using the different reference and higher quality additive, and/or using an adjusted operating condition). In the event of not obtaining the minimum performance deficit of the re-inoculated culture (e.g., the third culture), then the methods may further comprise confirming that the remedial measure (e.g., the higher quality test C1-containing substrate, and/or the higher quality additive, and/or the adjusted operating condition) supports the biological conversion process. In this manner, a number of remedial measures (e.g., progressively more highly purified C1-containing substrate) may be assessed, for example in a sequential manner, using the gas testing units described herein. According to some embodiments, the testing/evaluation methods may be complete when it is established/confirmed that at least one test C1-containing substrate quality, additive quality, and/or set of operating conditions supports the biological conversion process.

FIG. 1A depicts a side, cut-out view of a representative gas testing unit 1 having both a rear, "wet" or bioreactor stage-containing section 200 and a front, "dry" or analytical section 300. Preferably, these sections 200, 300 are separated by a barrier, such as vertical partition 250 that prevents or at least hinders the ambient environments surrounding the equipment housed in these sections from intermixing. A representative bioreactor 100 of a bioreactor stage in section 200 has a reactor volume generally in the range from about 0.25 to about 5 liters, and often from about 1 to about 3 liters. A typical length of a bioreactor, which holds this reactor volume (i.e., which contains the reactor gas and liquid phase contents), is from about 0.5 to about 1.5 meters. Normally, bioreactor-containing section 200 will include two separate bioreactor stages, as is more apparent from FIG. 1B, for the simultaneous evaluation of the performance of both reference and test CO-containing substrates.

A bioreactor stage in section 200 may further include an external liquid recycle loop 25 and an associated external recycle (or recirculation) pump 30 for improving mixing/uniformity within a given bioreactor 100 and/or improving the rate of vapor-liquid mass transfer. Using external liquid recycle loop 25, liquid product, including culture medium and a C1-fixing microorganism, may be withdrawn from a bottom section (i.e., proximate a bottom end) of bioreactor 100 (e.g., from below a gas distribution device, such as a sparger and/or from below a liquid inlet or a liquid outlet) and recycled externally to a top section (i.e., proximate an opposite, top end) of the bioreactor 100 (e.g., to above a gas/liquid interface that demarcates a boundary between a continuous gas phase zone and a continuous liquid phase zone). As described above, external liquid recycle loop 25 preferably operates without the added complexity required for separation and recycle of the C1-fixing microorganism, including membrane filtration systems and associated cleaning procedures. External liquid recycle pump 30 provides the external liquid circulation at a desired rate, for example at an optimum tradeoff between energy usage and mass transfer rate improvement. Other components associated with the mounting and control of bioreactor 100 may be included within bioreactor stage-containing section 200, for example shelving 201 and additional equipment external to bioreactor 100, such as that required for reactor temperature control (e.g., heat tracing and/or a fan for raising or lowering the temperature of bioreactor 100, as needed).

Analytical section 300 includes gas chromatography (GC) analyzer 301, including first and second chromatography columns 302a, 302b, configured, respectively, for analysis of both the gaseous and liquid products obtained from bioreactor stage 10. Such a configuration differs from the conventional use of high-pressure liquid chromatography (HPLC) for analysis of metabolite concentrations in liquid products. Although embodiments of the invention include the use of HPLC for liquid product analysis, it has been determined that space is advantageously conserved if the total analytical requirements of the gas testing unit are consolidated into a single GC analyzer. Generally, the columns used for analysis of the gaseous and liquid products contain different types of a stationary phase (e.g., a resin) for performing the desired chromatographic separations. Other equipment within analytical section 300 may include a high purity air generator ("zero air" generator, not shown) for use as a baseline gas source for the GC analyzer 301, enclosed electrical components 303, and operating software with the necessary display interface 304 (e.g., a computer), and a utility box 305. A satellite communication system 315 may also be included, for transferring data from the gas testing unit 1, particularly when in use at a prospective installation site with poor or unreliable communication service, to a second facility that may be remote from the site (e.g., at least 100 miles, at least 1,000 miles, or even at least 5,000 miles, away from the site). For example, the second facility may be the developer or licensor of the biological conversion process, having an interest in the operation of the gas testing unit in real time. Satellite communication system 315 may, therefore, transmit, to the second facility, information for use in providing operating instructions pertaining to the gas testing unit 1, such as recommended operating parameter adjustments or changes in, or the addition of, certain processing steps (e.g., gas pretreatment). According to other embodiments, satellite communication system 315 may allow direct control of the operation of gas testing unit 1, including the various operating parameters described herein. Further auxiliary components such as bottom drawers 306, benches (not shown), and/or a grille fan (not shown), may also be included in analytical section 300.

Figure 1B:
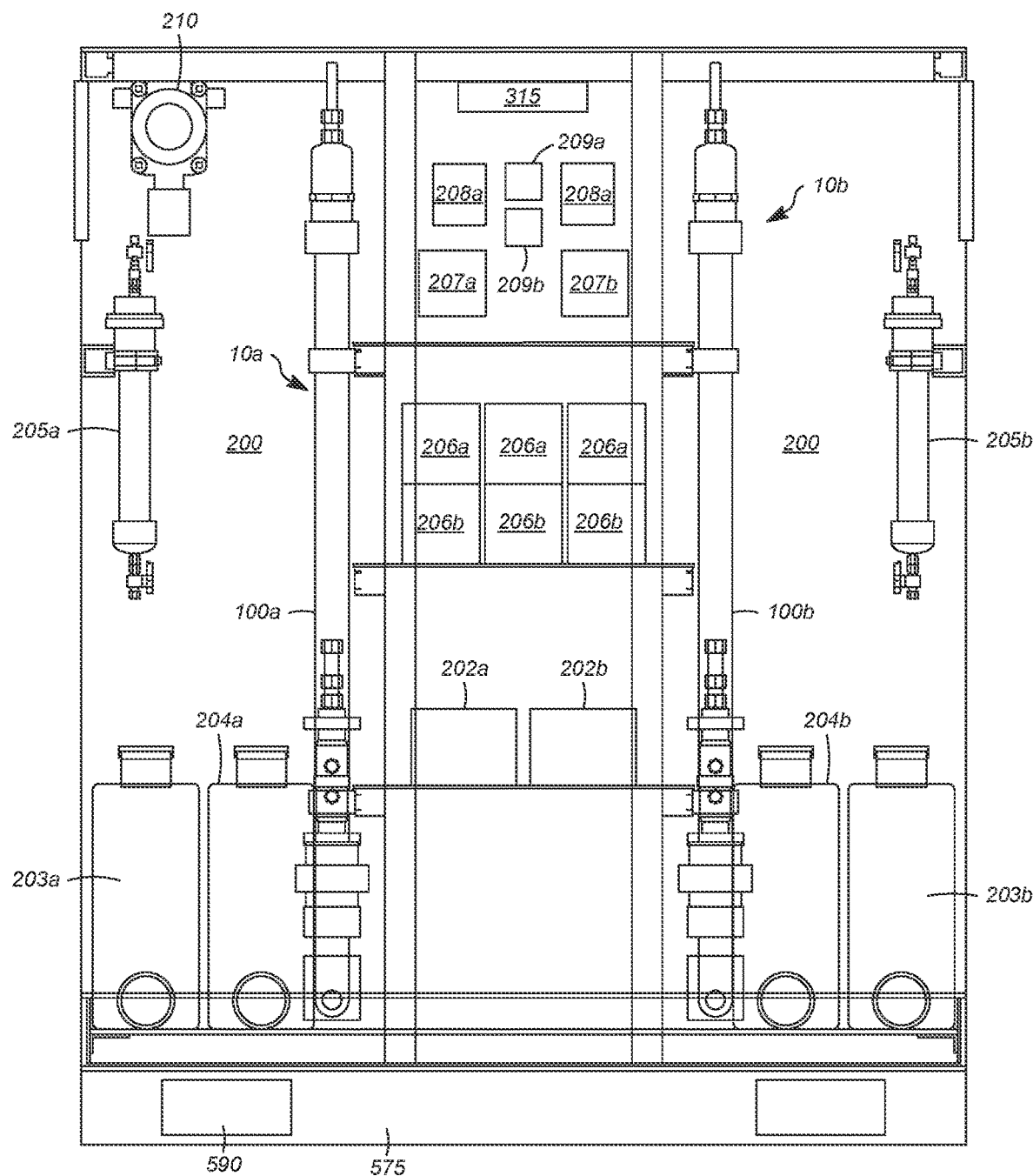

As shown in FIG. 1A, the components of gas testing unit 1 are housed within container 500, rendering it easily transportable to a remote location for on-site evaluation of a specific C1-containing substrate. This transportability advantageously avoids the potentially misleading (and costly) inaccuracies inherent in attempts to reproduce commercial gas streams, in terms of both composition and fluctuations in composition, at the site of a fixed laboratory, pilot plant, or demonstration unit. The depiction of an average size human 600 provides a representation of the typical dimensions of container 500. At the top covering analytical section 300, container 500 may have a connection such as a hinge connection 550 for opening the container to allow better access to equipment with analytical section 300. It should be appreciated that container 500 need not completely enclose gas testing unit 1, and openings, such as those needed for the operation of exhaust fans, may be provided in container 500. To the extent that container 500 includes open or exposed areas (or areas that may be opened), gas testing unit 1 is otherwise at least capable of being housed within a completely closed container having dimensions as described above. As shown in FIGS. 1A and 1B, container 500 may be transported on pallet 575 and moved relatively short distances via a forklift truck, engaging with forklift receiving openings 590.

The rear cut-out view of FIG. 1B illustrates two bioreactors 100a, 100b, of respective bioreactor stages 10a, 10b, for evaluating the performance of reference and test C1-containing substrates, respectively. Each of these bioreactors may be equipped with external liquid recycle loops 25, as described above with respect to FIG. 1A. FIG. 1B, therefore, provides a more complete view of the "wet" or bioreactor stage-containing section 200. In addition to, or alternative to, the operating control system used for regulating reactor temperature (described above), other operating control systems may be at least partly within section 200, although the instrumentation software associated with feedback control loops may preferably be included within analytical section 300. Such additional operating control systems may be used for controlling operating parameters such as fresh culture medium addition rate, gaseous C1-containing substrate feed rate, and reactor pH. In the case of controlling the surfactant addition rate, variable rate pumps 202a, 202b (e.g., syringe pumps) may be used for independently feeding surfactant to bioreactors 100a, 100b. In the case of controlling the gaseous C1-containing substrate feed rate, appropriate flow control valves may be used, which are sized according to the desired gas flow rate and the contemplated pressure upstream of the valve (supply pressure) and downstream of the valve (operating pressure). In the case of controlling reactor pH, the amount of a basic neutralizing agent introduced to a bioreactor stage (e.g., into recycle loop 25, shown in FIG. 1A) may be controlled with variable rate pumps. A representative pH control system is described in greater detail with respect to FIG. 2.

As shown in FIG. 1B, a total of six pumps are included, with three of these pumps 206a being used to convey basic neutralizing agent and other process liquids ($Na_2S$, media, etc.) to first bioreactor 100a, and the three other pumps 206b being used to convey such liquids to the second bioreactor 100b. Also housed within bioreactor-containing section 200 are displays and controllers relating to operating parameters associated with each bioreactor stage, including CO-containing substrate flow rate display/controllers 207a, 207b, fresh medium flow rate display/controllers 208a, 208b, and reactor temperature display/controllers 209a, 209b. These displays/controllers may be included on a fold-down panel (not shown) for ease of operator access/viewing. As described above with respect to the use of a satellite communication system in the analytical section, in an alternative embodiment satellite communication system 315 may likewise be present within bioreactor-containing section 200, with the same functionality as described above.

As further illustrated in FIG. 1B, equipment within bioreactor-containing section 200 includes that associated with direct handling of the feeds that are input to, and the products withdrawn from, bioreactors 100a, 100b. Examples of such equipment are fresh media containers 203a, 203b and liquid product waste containers 204a, 204b and their associated connections to bioreactors 100a, 100b. Further examples of equipment in this section are bubblers 205a, 205b that may serve various purposes. For example, in a particular embodiment, each bioreactor 100a, 100b may have a series of two or more bubblers in fluid communication with the gaseous products from these reactors. It is possible to use one or more empty bubblers directly downstream of each bioreactor as a protective measure against liquid overflow of the bioreactors. One or more fluid-filled bubblers may be used downstream of the one or more empty bubblers to provide a source of back pressure for diverting gaseous product to the GC when a gas sample is to be analyzed. Bioreactor-containing section 200 may further include an exhaust fan and vents (not shown) for allowing the circulation of fresh air into this section. This can hinder or prevent the accumulation of C1 carbons source (e.g. CO, $CO_2$, $CH_4$) in this section, in the case of leakage, to unsafe levels from the standpoint of a health risk or an explosion risk. In this regard, a safety control system, comprising a C1 gas detector 210 (e.g. CO detector), may also be included in bioreactor-containing section 200. The safety control system may be configured to override one or more, for example, all, of the operating control systems described above (e.g., for controlling the gaseous C1-containing substrate feed rate). For example, the safety control system may suspend the flow of the test C1 containing substrate and/or the reference C1-containing substrate, and preferably both, in response to a measurement of an ambient C1 concentration at above a threshold concentration (e.g., an alarm threshold concentration).

Figure 2:
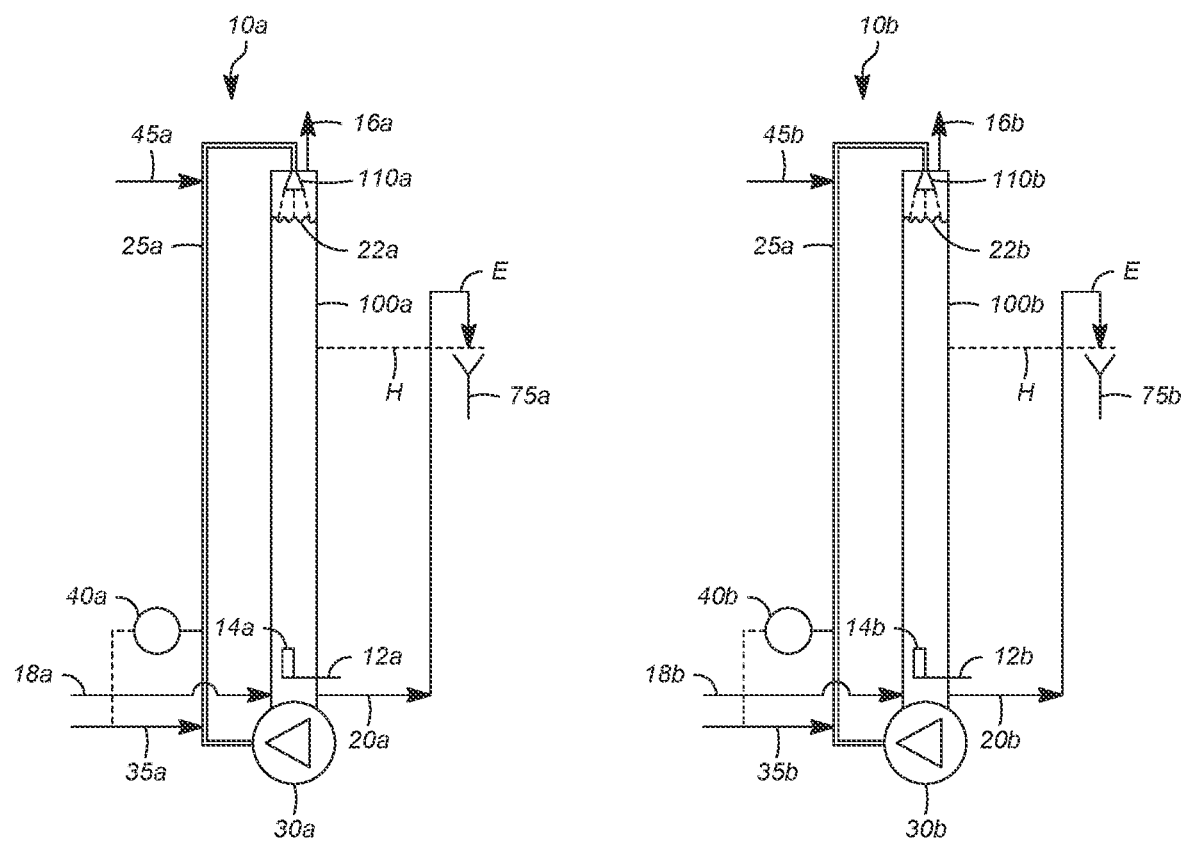
FIG. 2 depicts a close-up view of representative bioreactors for use in gas testing units as described herein and provides additional details relating to their operation.

FIG. 2 provides further details regarding the operation of bioreactors 100a, 100b, used for the comparative performance evaluation of reference and test C1-containing substrates, respectively. According to representative processes, these C1-containing substrates are fed to the bioreactor stages through gas inlets 12a, 12b positioned proximate the bottom ends of vertically extending bioreactors 100a, 100b of each bioreactor stage. For example, the gas inlets may extend into their respective bioreactors within the bottom 25%, and preferably within the bottom 10%, of the length of their respective bioreactors. The gas inlets will normally extend into their respective bioreactors, to gas distribution devices that may be disposed centrally within the bioreactors at a height corresponding generally to within these percentages of reactor length. Particular gas distribution devices include spargers 14a, 14b with which the gas inlets may be in fluid communication, proximate their respective first ends. Gaseous products, including unconverted C1 carbon source and any gaseous impurities of the C1-containing substrate (e.g., $H_2$), which are not utilized in the bioconversion reaction, are withdrawn from each bioreactor and exit through gas outlets 16a, 16b positioned proximate the top ends of the bioreactors, opposite the bottom ends. The gas outlets may extend into their respective bioreactors within the top 25%, and preferably within the top 10%, of the length of their respective bioreactors, or otherwise, gaseous products may be withdrawn from the tops of their respective bioreactors, without the gas outlets extending into their respective bioreactors at all.

Liquid product (or "broth") may be recycled through external liquid recycle loops 25a, 25b for example by pumping, using liquid recycle pumps 30a, 30b, from the bottom section of bioreactors 100a, 100b, from which liquid product is withdrawn, to the top sections of the bioreactors (e.g., to within the top 10% of the length of bioreactors 100a, 100b and to above liquid distribution device(s), such as shower heads 110a, 110b through which the liquid product is introduced into a continuous gas phase zone. This liquid then contacts gas that becomes disengaged at gas/liquid interfaces 22a, 22b and continues flowing upwardly (in bulk) through the continuous gas phase zone. In this manner, bioreactors 100a, 100b operate with countercurrent gas and liquid flows (upwardly flowing gas and downwardly flowing liquid) in this zone, which is disposed above continuous liquid phase zone, operating with internal liquid circulation as described above.

In defining locations of various features with respect to "reactor length," this length refers to that of the section containing the reactor contents (an admixture of reactants and reaction products), commonly considered as the "reactor volume," or "reactor working volume" and this length does not include process lines (e.g., feed inlet lines or product outlet lines) that may extend above or below the reactor volume, or sections of a column or other vessel that houses a reactor but does not contain any reactor contents. For example, in the case of a cylindrical reactor, the reactor length refers to the length of the axis of the cylinder. The "bottom 10%" of the reactor length refers to a range of heights, starting from the bottom of the reactor and extending upward for 10% of the reactor length. The "top 10%" of the reactor length refers to a range of heights, starting from the top of the reactor and extending downward for 10% of the reactor length.

Bioreactors 100a, 100b each include liquid inlets 18a, 18b, for the introduction of fresh culture medium and liquid outlets 20a, 20b for withdrawing liquid products of the reactors, which can be sampled to determine concentrations of ethanol and other metabolites, as well as concentrations of the C1-fixing microorganism, if desired. The transfer of fresh culture medium to, and liquid product (or "broth") from, each of the bioreactors 100a, 100b, via inlets and outlets 18a, 18b, 20a, 20b, may occur through small bore open pipes (e.g., having inner diameters from about 1 mm to about 6 mm) in fluid communication with these inlets and outlets. Liquid products, withdrawn from bioreactors 100a, 100b, may be passed to, and optionally extend above, height H, corresponding to the working, ungassed liquid level (i.e., a liquid level that would exist without gas hold-up). That is, the highest elevation E to which the final stage liquid product extends may be at or above height H. Height H may be adjustable and may correspond substantially to height H of siphon breakers 75a, 75b or another type of liquid take-off point. In the embodiment of FIG. 2, therefore, liquid product outlets 20a, 20b are in fluid communication with siphon breakers 75a, 75b that are adjustable in height, relative to bioreactors 100a, 100b. Elevation E and height H may be regulated to govern the liquid levels or hydraulic heads, i.e., the levels of gas/liquid interfaces 22a, 22b in their respective bioreactors 100a, 100b, independently.

In the specific embodiment depicted in FIG. 2, liquid inlets 18a, 18b and liquid outlets 20a, 20b are preferably positioned in a quiescent section below the respective gas inlets 12a, 12b and spargers 14a, 14b, to allow liquid to be fed to, and withdrawn from, this section or reactor location of a given bioreactor stage. It is also possible, however, for inlets and outlets to be positioned elsewhere along the length of their respective bioreactors, depending on the desired locations for the feeding and withdrawal of liquid products. In an alternative embodiment, for example, liquid outlets may be positioned at or near the levels of gas/liquid interfaces 22a, 22b, for example, to provide liquid level control based on overflow at the height of liquid withdrawal.

Conveniently, external liquid recycle loops 25a, 25b can provide locations of bioreactor liquid sampling/analysis, and also can be configured for bioreactor control. For example, a basic neutralizing agent (e.g., an aqueous base such as an $NH_4OH$ solution or a NaOH solution) may be added to these recycle loops through basic neutralizing agent inlets 35a, 35b as part of an operating control system for controlling reactor pH. The operating system can further include instrumentation for controlling the flow of the basic neutralizing agent, based on a measured reactor pH, and can more specifically include suitable feedback control loops associated with each of bioreactors 100a, 100b. Such control loops comprise, for example, pH analyzers 40a, 40b that measure (e.g., continuously or intermittently) the pH value of bioreactor liquid within external liquid recycle loops 25a, 25b. Such control loops also include the requisite hardware (e.g., control valves or variable rate feed pumps, not shown) and instrumentation software (e.g., computer programs) for comparing the measured pH value to a setpoint value for a given bioreactor, and then controlling the flow of basic neutralizing agent to achieve or maintain the set point.

Therefore, external recycle loops of the bioreactors 100a, 100b may be in fluid communication with respective basic neutralizing inlets 35a, 35b and comprise instrumentation for independently controlling pH within these bioreactors. External liquid recycle loops 25a, 25b may include instrumentation associated with the control of other operating parameters, such as reactor temperature. For example, temperature transmitters that measure (e.g., continuously or intermittently) the temperature of liquid within the external liquid recycle loops, with such temperatures being representative of operating temperatures of the bioreactors, may be used to regulate the operation of heat tracing and/or a fan, described above, for reactor temperature control. Additionally, external liquid recycle loops 25a, 25b may include further liquid inlets 45a, 45b for introducing other liquid diluents, reagents (e.g., surfactants), and/or nutrients, to the bioreactors 100a, 100b independently at the same or varying rates.

The bioreactor stages 10a, 10b may therefore have independently controllable process operating variables, the control of which may involve sampling/analysis of bioreactor liquid product on the external liquid recycle loops 25a, 25b, as described above, and/or the introduction of fresh culture medium, basic neutralizing agent, and/or other process liquids through any of inlets 18a, 18b, 35a, 35b, 45a, 45b. Representative process operating variables include fresh culture medium addition rate, gaseous C1-containing substrate feed rate, reactor temperature, reactor pH, and combinations thereof. According to various other exemplary control methodologies, (1) the flow of the C1-containing substrate (e.g., the flow of reference C1-containing substrate to bioreactor stage 10a and/or the flow of test C1-containing substrate to bioreactor stage 10b) may be controlled based on the measured reactor pH, (2) the flow of basic neutralizing agent to either or both of bioreactor stages 10a, 10b may be controlled based on a measured acidic metabolite concentration (e.g., acetate concentration) in the corresponding bioreactor liquid product, and/or (3) the flow of fresh culture medium to either or both of bioreactor stages 10a, 10b may be controlled based on a measured concentration of the C1-fixing microorganism in the corresponding bioreactor liquid product.

The gas testing units described above may be used in methods for evaluating a test C1-containing substrate, for example, available at a prospective installation site for a commercial scale biological conversion process. First and second bioreactors may be used for processing, respectively, a reference C1-containing substrate (e.g., a C1 carbon source-containing gas of a known composition that may be fixed throughout the duration of the evaluation method) and the test C1-containing substrate, which may be the available C1-containing waste gas from an industrial facility, such as a steel manufacturing facility, optionally pretreated to remove one or more contaminants. In general, pretreating is performed to remove one or more contaminants of the test C1-containing substrate, or at least a portion of the one or more contaminants (e.g., at least 75%, at least 90%, or at least 99%, of the one or more contaminants) that are detrimental to the biological conversion process (e.g., are harmful to the growth of the C1-fixing microorganism). Typically, contaminant(s) in the test C1-containing substrate, which are removed by pretreating, are those that, in the absence of the pretreating, would contribute to an observed performance deficit in the biological conversion process, when compared to the same process being performed, under the same conditions. Contaminants include hydrocarbons (e.g., benzene) and heteroatom-containing hydrocarbons (e.g., halogenated hydrocarbons or hydrocarbons containing at least one of Cl, O, N, and/or S, such as dichloropropane, epichlorohydrin, and dioxins). Any of such contaminants are generally present in minor amounts (e.g., in an amount of less than 1%, less than 1000 ppm, less than 100 ppm, or even less than 10 ppm, by volume) in the untreated, test C1-containing substrate. Exemplary pretreating includes contacting the test C1-containing substrate with a solid material or liquid scrubbing medium that selectively removes one or more contaminants, for example by adsorption or dissolution. Representative solid materials include carbon (e.g., activated charcoal), resins, and zeolites. Other contaminants include dust particles and other solids (e.g., catalyst fines) that may be removed by filtration and/or a liquid scrubbing medium.

A representative reference C1-containing substrate may be pure CO, or a synthetic blend of CO and one or more other gases (e.g., a $CO/H_2$ blend, or a CO, $CO_2$, and $H_2$ blend). The one or more other gases may be gases known to be present in the test C1-containing substrate at approximately the same concentrations. A synthetic blend may be representative of a composition for which performance data has previously been obtained, and optionally correlated with the performance of a larger-scale operation. In this manner, the comparative performance of the reference C1-containing substrate with the test C1-containing substrate may be used to calculate a predicted performance of the latter, at the larger-scale operation, for example, a pilot plant scale, demonstration scale, or commercial-scale operation. In many cases, a reference C1-containing substrate, including pure CO or a synthetic blend of CO, may be supplied and fed to one or both of the bioreactors from a pressurized cylinder. Using a suitable pressure regulating valve (or series of valves), the pressure downstream of the cylinder may be reduced to the operating pressure of the bioreactors (e.g., from 0 to 5 bar absolute pressure).

The performance of the first and second bioreactors, processing the reference and test C1-containing substrates, respectively, may be determined and compared, as a basis for establishing the suitability of the test C1-containing substrate. For this purpose, a gas testing unit as described herein may be configured for analyzing both gaseous and liquid products of the first and second bioreactors. For example, the gaseous products may be analyzed to determine the amount of remaining C1 gas, following consumption by the bacterial culture, of C1 gas in the reference and test C1-containing substrates. The overall substrate utilization of a bioreactor refers to the percentage of the substrate that is input to that bioreactor and utilized in the conversion to desired product(s) (e.g., ethanol) and other metabolites of the microorganism. Using a CO-containing gas as an example, if the composition of the gaseous product exiting the bioreactor is determined, then the overall CO utilization (expressed as a fraction) may be calculated as:

1−(rate of CO exiting the bioreactor)/(rate of CO input to the bioreactor).

The gas testing unit can provide, or can at least provide sufficient information (e.g., feed and product gas flow rates and compositions) for, a determination of C1 carbon utilization in each of the bioreactors, as one performance parameter for comparison between these bioreactors. This C1 carbon source utilization is determined on a "per pass" or "once-through" basis, without accounting for the use of gaseous product recycle (and added expense) that can provide higher total utilization values. However, the per pass C1 carbon utilization can be used in modeling to predict total C1 carbon utilization of a process utilizing such recycle.

Other analytical results from the gas testing unit can be used in the comparison of performance between bioreactors operating with the reference and test C1-containing substrates. For example, liquid products obtained from these bioreactors can be analyzed, typically after separation of the C1-fixing microorganism (e.g., by filtration) to determine the concentrations (titers) of ethanol and other metabolites, including acetate and 2,3-butanediol. Using the GC analyzer, for example, all of these concentrations may be obtained in grams per liter, g/l. In some cases, a suitable analytical device may be included with the gas testing unit, or otherwise used separately for the measurement of C1-fixing microorganism concentration in the liquid product. Representative devices include those measuring the absorbance or transmission of electromagnetic energy through the sample (e.g., a spectrophotometer), a certain biological activity of the sample (e.g., a plate reader), or another property of the sample (e.g., impedance/capacitance) in a disposable or reusable probe (e.g., an on-line biomass probe). Analysis of the gaseous and liquid products may be performed continuously (e.g., using an online analyzer) or intermittently. Analysis may also be conducted automatically or manually, with manual injection into an analyzer, such as a GC, often being preferred due to flexibility in sample preparation and a reduction in equipment requirements. For example, sampling systems for the automated analysis of liquid products of the bioreactors can include suitable conduits (e.g., tubing or piping), valves, pumps, and actuators to allow sampling of the desired bioreactor at the desired time, and suitable devices for flushing (purging) sample lines to obtain accurate results. In view of these considerations, and according to particular embodiments, analysis of gaseous products may be performed automatically, and analysis of the liquid product may be performed manually.

The analysis of the gaseous and liquid products of the bioreactors over time allows for the monitoring of one or more performance parameters, used as a basis for establishing the suitability of a given test C1-containing substrate, optionally having been subjected to pretreating as described above. The comparison of the performance of the first bioreactor (processing reference C1-containing substrate), relative to the performance of the second bioreactor (processing test C1-containing substrate) may generally involve assessing whether one or more measured performance parameters deviates substantially (i.e., exhibits a performance deficit or offset) with respect to the second bioreactor (or bioreactor culture), relative to the first bioreactor (or bioreactor culture). The performance of the bioreactors may be compared, for example, over a simultaneous period of operation, or test period, as described herein. To obtain sufficient data regarding the performance over the operating periods of the first and second bioreactors (i.e., the time periods over which these bioreactors are fed the reference and test C1-containing substrates, respectively), gaseous and liquid products of the bioreactors may be analyzed, if not continuously, then intermittently over the respective bioreactor operating periods at sufficient sampling intervals. Representative sampling intervals range from about 15 minutes to about 10 hours and are normally from about 30 minutes to about 8 hours. According to a particular embodiment, gaseous products are sampled and analyzed at intervals ranging from about 30 minutes to about 2 hours, and liquid products are sampled and analyzed at intervals ranging from about 4 hours to about 8 hours. Preferably, gaseous and liquid product samples are taken and analyzed at substantially constant intervals, during the bioreactor test periods.

As described above, one performance parameter that may be compared between the bioreactors is C1 carbon source utilization. Other performance parameters include the ethanol concentration (titer) in the liquid products of the bioreactors and/or the concentrations of one or more metabolites (e.g., acetate) in these liquid products. A further performance parameter is the ratio of ethanol to a given metabolite (e.g., the ethanol/acetate weight ratio) in the liquid products. Suitability of a given test C1-containing substrate may be established if one or more of these performance parameters are not substantially different with respect to the second bioreactor (or bioreactor culture), relative to the first bioreactor (or bioreactor culture). The threshold level of difference that may be tolerated, according to some embodiments, can be quantified in terms of a minimum performance deficit (or offset) of the second bioreactor, relative to the first bioreactor.

For example, in the case of the performance parameters described above, a performance deficit may be based on the average value of the performance parameter over the test period (e.g., the average value of the C1 carbon source utilization measured in the first bioreactor, compared to that of the second bioreactor). A minimum performance deficit can be, for example, at least a 5% deficit, at least a 10% deficit, at least a 15% deficit, or at least a 20% deficit in the average value of the measured performance parameter. As would be apparent to those skilled in the art, having regard for the present specification, other specific minimum performance deficits (e.g., any value in the range from at least a 1% deficit to at least a 75% deficit) can be used to quantify the threshold difference that may be tolerated to establish suitability, depending on the particular performance parameter and other factors. As would also be apparent to those skilled in the art, having regard for the present specification, a "deficit" refers to a decrease in the performance of the second bioreactor, relative to the first bioreactor, for example (1) a percentage reduction in average C1 carbon source utilization of the second bioreactor, relative to the first bioreactor, (2) a percentage reduction in average ethanol concentration in liquid products of the second bioreactor, relative to those of the first bioreactor, (3) a percentage increase in average concentration of acetate or other metabolite in liquid products of the second bioreactor, relative to those of the first bioreactor, or (4) a percentage reduction in the average ratio of ethanol to a given metabolite (e.g., acetate) in liquid products of the second bioreactor, relative to those of the first bioreactor.

According to other embodiments, a performance deficit may be based on the rate of change of the performance parameter over the test period (e.g., the rate of change of the C1 carbon source utilization measured in the first bioreactor, compared to that of the second bioreactor), and therefore the minimum performance deficit can reflect a desired degree of stability to be achieved using the test C1-containing substrate. A rate of change can be expressed as an average difference in the measured performance parameter per unit time (e.g., average % C1 carbon source utilization loss/day), or otherwise expressed in terms of a rate constant obtained from fitting the measured values of the performance parameter to a model equation, such as an exponential rate equation (e.g., an exponential decay equation, or first order or higher order reaction rate equation, or kinetic expression). In such cases in which a rate of change is used as the basis for a given performance deficit, the representative, minimum performance deficits as described above (in terms of percentages) are still applicable. Also, in such cases, a "deficit" again refers to a decrease in the performance of the second bioreactor, relative to the first bioreactor, for example (1) a percentage increase in the average rate of C1 utilization loss, or associated decay rate constant, of the second bioreactor, relative to the first bioreactor, (2) a percentage increase in average rate of ethanol concentration loss, or associated decay rate constant, in liquid products of the second bioreactor, relative to those of the first bioreactor, (3) a percentage increase in the average rate of increase in the concentration of acetate or other metabolite, or associated rate constant, in liquid products of the second bioreactor, relative to those of the first bioreactor, or (4) a percentage increase in the average rate of decrease in the ratio of ethanol to a given metabolite (e.g., acetate), or associated rate constant, in liquid products of the second bioreactor, relative to those of the first bioreactor.

Other performance parameters, or other changes in performance parameters, may be used as a basis for establishing the suitability of a given test C1-containing substrate, as would be appreciated by those skilled in the art, having regard for the present specification. Normally, the comparison between the performances of the bioreactors, used as a basis for establishing suitability of a test C1-containing substrate, comprises measuring at least the concentrations of at least one C1 carbon source in the gaseous products of the first and second bioreactors and measuring concentrations of ethanol and at least one further metabolite (e.g., acetate) in the liquid products of these reactors. In many cases, the compositions of the reference C1-containing substrate, used for feeding the first bioreactor, is known and therefore not analyzed on a continuous or even a periodic basis during the test period. This may also be true in the case of the test C1-containing substrate, at least over some limited duration of operation (e.g., ranging from about 1 to about 5 days), which may correspond to a test period. According to other embodiments, the composition of the test C1-containing substrate may fluctuate significantly during the test period, and indeed such fluctuations may be valuable for assessing performance under a realistic composition range that would be encountered in commercial practice. In particular embodiments, the concentration of the C1 carbon source or other gases in the test C1-containing substrate may fluctuate by at least about 20% (e.g., from about 20% to about 500%), based on 100%×(the highest concentration/the lowest concentration−1), in which the highest and lowest concentrations are those measured during the test period. In other embodiments, this deviation may be at least about 40% (e.g., from about 40% to about 250%), of at least about 50% (e.g., from about 50% to about 100%).

Figure 3:
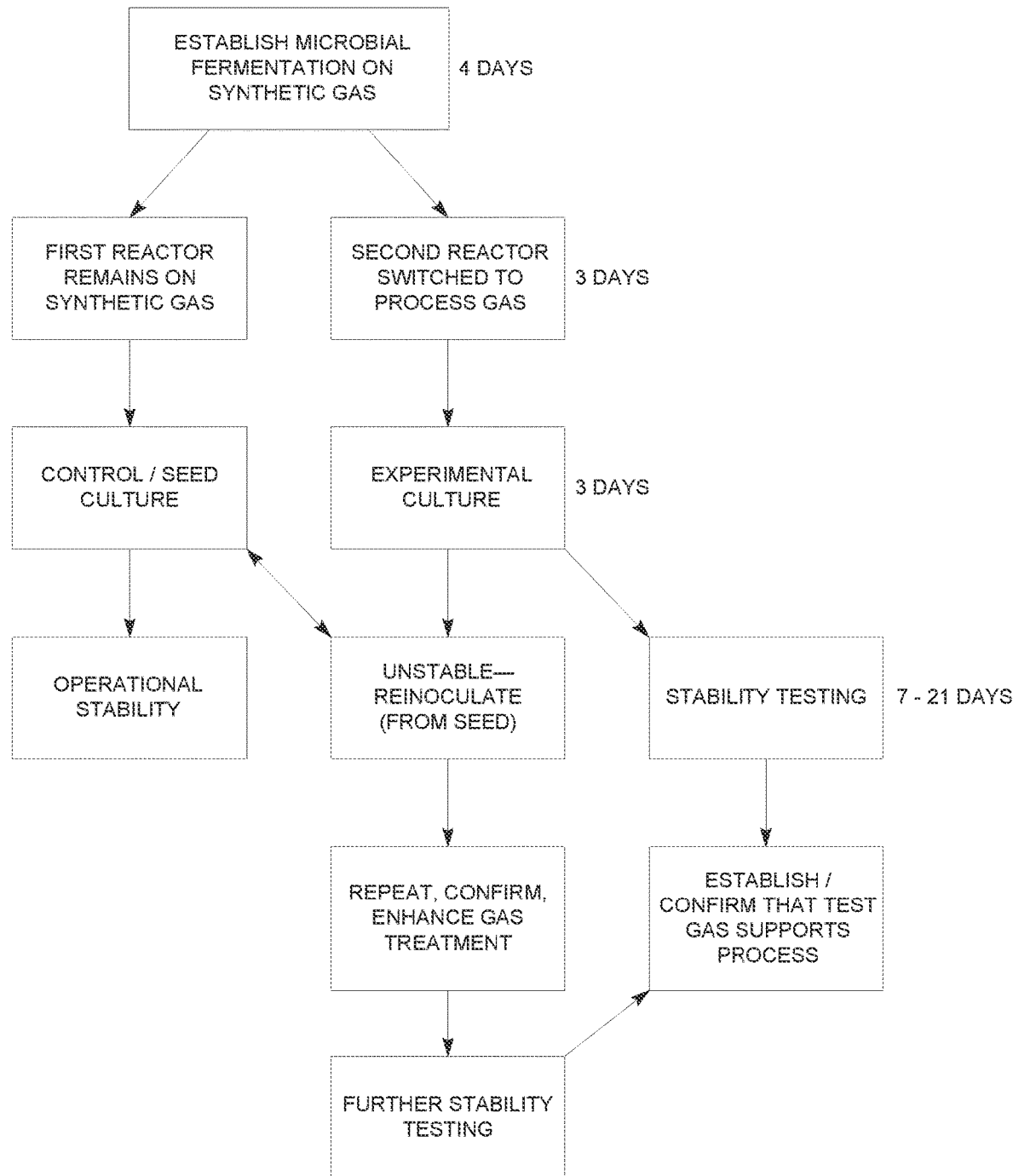
FIG. 3 is a flowchart illustrating a representative methodology, which may be performed with gas testing units as described herein, for determining whether a test C1-containing substrate, optionally following one or more remedial measures as described herein (e.g., increasing its purity), is suitable for a biological conversion process.

According to the specific method depicted in FIG. 3, the biological conversion process, for example microbial fermentation for the production of ethanol from C1-carbon source using a C1-fixing microorganism, is established in both the first and second bioreactors using the reference C1-containing substrate (e.g., a synthetic gas, which may be a blend of gases, as described above). In this step, the separate, first and second cultures of the C1-fixing microorganism are maintained, utilizing the reference C1-containing substrate as a nutrient for both cultures. According to one possible procedure for initiating the process, the first and second bioreactors may be inoculated or charged with C1-fixing microorganism initially (e.g., in freeze-dried form), and, after a period of batch growth in culture, the microorganism may achieve a sufficiently high concentration, such that continuous addition of fresh culture medium can be initiated.

In representative embodiments, the culture is established, for example by batch and then continuous operation, for a total period of 4 days, or more generally from about 1 day to about 10 days, for example from about 2 days to about 7 days. After this period, the reference C1-containing substrate, having been fed to the second bioreactor, is changed to the test C1-containing substrate (process gas), whereas the reference C1-containing substrate is continually fed to the first bioreactor. Operation of the first bioreactor is maintained with a stable bacterial culture ("control/seed culture") that may be used, if necessary, to seed or re-inoculate the second bioreactor, in the event of poor/unstable operation of this bioreactor. The first bioreactor, having the "control/seed culture," is operated during the period of assessing the performance of the second culture, relative to that of the first, e.g., by comparing one or more of the performance parameters described above, based on analytical results obtained from the gaseous and liquid products of the bioreactors.

As shown in FIG. 3, steady-state operation in the second bioreactor, following the switch from reference to test C1-containing substrate, can require 3 days, or, more generally, from about 1 to about 7 days. The test C1-containing substrate can be fed to this "experimental culture," under steady state testing (evaluation) conditions, for an additional 3 days, or, more generally, for an additional 1 to 7 days of a representative testing period. To confirm the suitability of the test C1-containing substrate, an additional period of "stability testing" may be performed, with the frequency of analysis of the gaseous and liquid products being the same as in, or perhaps decreased relative to, that of the preceding performance assessment of the "experimental culture." The confirmatory stability testing period may last, in representative embodiments, from about 3 days to about 28 days, and typically from about 7 days to about 21 days. Therefore, the second bioreactor may be monitored for performance with the experimental culture, during the time that steady-state conditions are established for this culture, and/or during the subsequent period of stability testing. In the event that instability is encountered during either or both of these periods, or in the event that a minimum performance deficit, as described above, is obtained (i.e., a minimum tolerable level of deficit of a performance parameter, as described above, is exceeded), the second bioreactor may be seeded or re-inoculated. In the event that no instability (or a minimal or tolerable level of instability) is encountered, or in the event that a minimum performance deficit, as described above, is not obtained (i.e., a minimum tolerable level of deficit of a performance parameter, as described above, is not exceeded), then it can be established or confirmed that the test C1-containing substrate is suitable for the biological conversion process.

If it becomes necessary for the second bioreactor to be seeded or re-inoculated (e.g., with a third bacterial culture) a remedial measure, as described above, may be tested, followed by repeating the steps, with respect to the second bioreactor, of achieving steady-state operation, conducting performance assessment relative to the first bioreactor, and/or performing stability testing. A representative remedial measure is a higher quality (e.g., purer) test C1-containing substrate, obtained following enhanced gas treatment (purification), prior to introduction to the second bioreactor. Testing of the remedial measure may involve a performance assessment based on obtaining the same or a different minimum performance deficit, as in the original testing. As illustrated in FIG. 3, a period of "further stability testing" may be performed to establish or confirm that the remedial measure is suitable for the biological conversion process. Conditions and duration of the further stability testing may be the same or different, relative to those of the original stability testing. As will be appreciated by those skilled in the art, having regard for the present specification, testing of further, successive remedial measures (e.g., using fourth, fifth, sixth, etc., bacterial cultures) may be performed, particularly in the event that prior remedial measures are not successful.

The following examples are set forth as representative of the present invention. These examples are not to be construed as limiting the scope of the invention, as these and other equivalent embodiments will be apparent in view of the present disclosure and appended claims.

Example 1

Unit Configuration

A gas testing unit was constructed, having a bioreactor section, including two circulated loop reactors (2 liters in reactor volume each). The control of C1-containing substrates (reference and test) was based on gas flow meter/controller settings, and an automatic pH compensation (control) system was included for each reactor, based on the adjustment of $NH_4OH$ or other basic neutralizing agent flow. The reactor stages did not include membrane separation systems for the separation and recycling of the bacterial culture. Heat tracing and a fan were installed in the bioreactor section for reactor temperature control. Equipment in the analytical section, maintained apart from the bioreactor section using a vertical partition, included a dual column gas chromatograph (separate GC columns for gas and liquid samples) and valves/actuators to allow for automated sampling for gas analysis. The analytical section was configured for manual injection into the GC of liquid products from the reactors, for determination of the concentrations of ethanol, acetic acid (acetate), and 2,3-butanediol. A laptop computer was included in this section for control of the analytics and process operating parameters.

More specifically, the gas chromatograph was customized with an external oven, valves, actuators, and a 6-port selection valve to allow for the automated and continuous analysis of gaseous products. This valve was controlled by the software that also controlled the GC and that was executed by the laptop computer. Only the valves and sample holding loop were configured external to the main GC oven; other column components were located in the oven. Segregation of the actuators and valves from the oven was chosen as a way to prevent thermal expansion and contraction and thereby prolong the operating lifespan and reduce maintenance. The width of the GC and its supporting components was approximately 80 cm. Other equipment for use with the GC included a zero-air generator, a thermal conductivity (TCD) detector (to be run with high purity pure argon), and a flame ionization detector (FID) (to be run with compressed air and hydrogen).

The bioreactor and analytical sections (including the GC and its supporting components, with approximately 10 cm around its periphery to allow cooling) were fit into a self-contained box for transport. Pretreatment of the C1-containing substrate, using for example activated carbon, was considered an "outside the box" option, depending on the customer's gas quality. For additional control/minimization of temperature fluctuations, the gas testing unit could be housed indoors (e.g., within a temporary building).

Example 2

The Gas Testing unit of Example 1 was sent to a customer site to facilitate testing of the customer C1-containing substrate (test C1-containing substrate). The C1-containing gas to be tested was as industrial gas produced as a major by-product of a phosphorus production process. Typically, the C1-containing as was being flared by the customer. The gas testing unit was sent to the site to determine whether the test C1-containing substrate was suitable for conversion to products by a biological conversion process.

The composition of the test C1-containing substrate is shown in table 3.

TABLE 3

| Bulk Composition | | | | Known Contaminants (ppm) | | | |
|---|---|---|---|---|---|---|---|
| CO | $N_2$ | $CO_2$ | $H_2$ | $PH_3$ | $H_2S$ | $P_2O_5$ | $P_4$ |
| 72% | 20% | 1% | 6% | 1200-1400 | 0-1000 | 1000-2000 | 300-1000 |

Gas clean-up of the test C1-containing substrate typically involved passing the test C1-containing substrate through an electrostatic precipitator and water scrubber. The test C1-containing substrate was further treated to remove known contaminants. The further treatment included the use of two foam scrubbers and an activated carbon bed. The first foam scrubber contained a sodium carbonate solution (5%), the second foam scrubber contained a copper sulfate solution, and the carbon bed contained approximately 10 kg "sulfisorb 8 GAC" from Calgon.

A compressed air gas booster was used to increase the pressure of the treated test C1-containing substrate to provide to a minimum of 2.0 barg at the inlet of the gas testing unit.

Three test runs were performed at the customer facility to assess the suitability of the test C1-containing substrate. Test runs 1 and 2 were performed using a treated test C1-containing substrate, and Test 3 was performed using a raw/untreated test C1-containing gas.

Test run 1 was performed using a treated test C1-containing substrate having the following composition:

| CO | $PH_3$ (ppm) | $H_2S$ (ppm) | $P_2O_5$ (ppm) | $P_4$ (ppm) |
|---|---|---|---|---|
| 60% | 1.0-1.8 | 53 | 15-60 | 20 |

Liquid nutrient media was added to the GTS reactor vessel. The liquid nutrient media contained, per liter, MgCl, $CaCl_2$ (0.5 mM), KCl (2 mM), $H_3PO_4$ (5 mM), Fe (100 μM), Ni, Zn (5 μM), Mn, B, W, Mo, and Se (2 μM). The media was autoclaved, and after autoclaving, the media was supplemented with thiamine, pantothenate (0.05 mg) and biotin (0.02 mg) and reduced with 3 mM cysteine-HCl.

Nitrogen gas is sparged into the reactor vessel, and the pH and ORP are adjusted. The GTS reactor vessel is then inoculated with freeze-dried cells through a syringe. The freeze-dried cells were *Clostridium. autoethanogenum* strain DSM23693 deposited at DSMZ (The German Collection of Microorganisms and Cell Cultures, Inhoffenstraße 7 B, 38124 Braunschweig, Germany). The input gas is then switched from nitrogen gas to the treated C1-containing gas.

The test run was performed over a period of 5 days. At day 4.2 growth of the *Clostridium autoethanogenum* culture was confirmed visually. At day 5, GC analysis of the fermentation broth confirmed an ethanol concentration of 1.6 g/L and an acetate concentration of 5.4 g/L.

Test run 1 confirmed the successful revival of the freeze-dried inoculum, demonstrated continuous growth of the culture and demonstrated ethanol production by the culture. Test run 1 confirmed that the treated test C1-containing substrate was suitable for the biological process, and demonstrated that no unknown contaminants, which have a negative impact on growth, were present in the test C1-containing substrate.

Test run 2 was performed using a treated C1-containing substrate having a 13% CO composition. Visual confirmation of growth was confirmed on day 3.75. At day 4.75, a relatively stable acetic acid concentration of 5-6 g/L was shown, with no concurrent ethanol production. This result is consistent with undersupplied culture conditions. The CO composition of the incoming test C1-containing was increased to a concentration of 72% on day 9.73. Over the next 3 days, ethanol production was observed, with measurements of greater than 8 g/L of ethanol observed.

Test run 2 confirmed the findings of Test run 1.

Test run 3 was started using treated test C1-containing gas having a CO composition of 72%. Once growth of the culture had been determined, the gas was switched to an untreated test C1-containing substrate. The culture collapsed within a day of the untreated test C1-containing being supplied to the gas testing unit. Test run 3 confirmed that the raw/untreated test C1-containing gas is not suitable for the biological process.

Unit Operation/Auxiliary Equipment

Both bioreactors would be charged (inoculated) with freeze-dried organisms, and the cultures established using synthetic gas, such as cylinder gas from a local supplier. Following the start-up with synthetic gas, one reactor would be switched to site gas to validate performance on stream, for a testing period of several days to several weeks. If the site gas is not available at sufficient pressure, e.g., nominally at least about 2 bar absolute pressure, for example in a range from about 3 to about 10 bar absolute pressure, a booster compressor may be used as needed to increase the available pressure of the site gas to such pressures, thereby ensuring a stable input to the bioreactors. A valve used for switching the source of gas to a bioreactor, from synthetic gas (e.g., bottled or cylinder gas) to site gas, may in some cases have additional ports for allowing gas flow from alternative sources. For example, a 3-way valve may allow an operator to alter the source from among a synthetic gas, site gas, and a purge gas, which may be an inert gas such as nitrogen. Optional batch runs could be performed to investigate increasing the ethanol titer of the liquid products. Due to the low projected gas flow rates (on the order of 2 liters/minute) needed for the testing, the gaseous products exiting the gas testing unit could be either returned to their source (e.g., the customer's waste gas stream) or otherwise vented to the atmosphere.

An exemplary listing of equipment, auxiliary materials, and support to be included with the gas testing unit, as well as equipment/requirements of the prospective facility (customer) and further requirements from local vendors, as needed for implementation/operation of the gas testing unit, is as follows:

| Included with Gas Testing Unit | Prospective Facility | Local Vendors |
|---|---|---|
| Compressor (if required) | Site gas at nominal 5 Bar pressure | Synthetic gases ($N_2$, CO, Argon, Hydrogen) |
| Microbes | | |
| 1x staff support | Vent (or return to the origin) | |
| Media (in powder form) | Housing (air-conditioned) | Analytics (GC-MS) laboratory |
| Glassware | Water | |
| Chemicals (supplied in pre-packs) | Waste disposal | |
| | Gas treatment (optional) | |
| Gas treatment (optional) | Information regarding site gas: composition fluctuations, contaminant identity, and concentrations. $CO_2$ fire extinguisher Table | |
| Operating Instructions/Manuals | | |
| Biomass probes (optional) | | |
| General laboratory consumables (syringes, tubes, needles, filters, etc.) | | |

Capabilities/Objectives/Deliverables

Some key capabilities associated with the operation of the gas testing unit include the verification of (1) stable and otherwise acceptable operation throughout a range of changing gas compositions supplied by the facility, (2) positive microorganism growth on untreated gas, (3) the contaminant profile of gas and liquid samples, (4) performance targets obtained elsewhere (in off-site testing) using a synthetic blend, (5) any operating discrepancies caused by the use of site gas versus synthetic gas and/or the use of process (local, on-site) water versus tap (local, potable) water and also versus purchased, distilled water.

Further objectives of the on-site testing of gas from a prospective facility are (1) to obtain a comparison of bioreactor performance with site gas, either with or without pretreating, and process water, versus synthetic gas, (2) to assess the impact of gas contaminants including trace compounds, in aggregate, on gas uptake, microorganism growth, and metabolite selectivity, relative to synthetic gas without contaminants, (3) to assess the impact of site process water, similarly, (4) to assess whether further gas cleanup/pretreatment is required, (5) to assess whether local process water will support bacterial growth at various rates of diluent (fresh medium) introduction, (6) to verify or update reactor models with the data obtained and thereby improve performance estimates as a basis for providing guarantees, (7) to obtain a "post-mortem" analysis of gas contaminants, desorbed from gas pretreatment beds (adsorbent beds), for example by comparison to known contaminants.

Key deliverables to be provided, as a result of information gained from the gas testing unit, were expected to vary and depend on the needs of the project and prospective facility. Some representative examples of deliverables are verification that (1) the facility provides a gas stream that supports the biological conversion process, (2) product (ethanol) and metabolite selectivity's are acceptable from an economic standpoint, (3) proposed gas purification strategies (if used) are effective, (4) process water or another local water source is acceptable, (5) the range of gas composition fluctuations can be tolerated and their influence predicted, (6) the GC analyses and other information of the gas testing unit is accurate, (7) gas contaminant levels (if detected) can be tolerated by the microbial culture.

Overall, aspects of the invention are directed to transportable units for the on-site testing of the actual gas, generated at a prospective facility, for use in biological conversion processes, and particularly for the microbial fermentation of CO-containing substrates for ethanol production. The gas testing units and associated methods and methodologies for establishing the suitability of a test CO-containing substrate provide a number of advantages as described herein, particularly with respect to obtaining realistic and accurate performance expectations and objectives, which could not otherwise be obtained from attempts to simulate a commercial gas composition off-site. Those having skill in the art, with the knowledge gained from the present disclosure, will recognize that various changes can be made in the apparatuses and methods described herein, without departing from the scope of the present invention.

The invention claimed is:

1. A method comprising:
feeding a C1-containing substrate from a source to a fermentation system comprising bioreactor stage comprising a C1-fixing microorganism in a culture medium to produce products selected from alcohols and acids, wherein the fermentation system is capable of being housed within a container having a volume of less than about 6 $m^3$ and transportable to multiple locations, the process characterized in that that it is carried out at a site of the source of the C1-containing substrate.

2. The method of claim 1, wherein the C1-containing substrate obtained from the source has been pretreated to remove a contaminant.

3. The method of claim 1, wherein the culture medium is prepared with, or supplemented with, a local water source.

4. The method of claim 1, wherein the test C1-containing substrate contains at least one C1-carbon source selected from the group consisting of CO, $CO_2$, and $CH_4$.

5. The method of claim 1, wherein the C1-fixing microorganism is a carboxydotrophic microorganism from the genus *Clostridium*.

6. The method of claim 5, wherein the C1-fixing microorganism is selected from the group consisting of *Clostridium autoethanogenum*, *Clostridium ljungdahlii*, and *Clostridium ragsdalei*.

7. The method of claim 1 where the fermentation system is capable of being housed within a box having length, width, and height dimensions of less than about 1.8 meters each.

8. The method of claim 1 wherein the bioreactor stage comprises a circulated loop bioreactor.

9. The method of claim 1 wherein the fermentation system further comprises an operating control system for controlling one or more operating parameters selected from the group consisting of fresh culture medium addition rate, gaseous C1-containing substrate feed rate, reactor temperature, and reactor pH.

10. The method of claim 9 wherein the one or more operating parameters include reactor pH, and the control system includes instrumentation for controlling the flow of a basic neutralizing agent to the bioreactor, based on a measured reactor pH.

11. The method of claim 1 where the fermentation system further comprises a safety control system for suspending flow of at least the C1-containing substrate in response to a measurement of an ambient C1-containing substrate concentration at above a threshold concentration.

12. The method of claim 1 where the source of the C1-containing substrate is selected from an steel manufacturing processes, non-ferrous product manufacturing, petroleum refining processes, biofuel production, coal and biomass gasification processes, electric power production processes, carbon black production processes, ammonia production processes, methanol production processes, coke manufacturing processes, and syngas production processes.

13. A fermentation unit, comprising:
a vertically extending bioreactor vessel comprising a gas inlet port and a gas outlet port, the gas inlet port located proximate to the bottom end of the vertically extending bioreactor, the inlet gas port in fluid communication with piping means, said piping means in fluid communication with an industrial facility and configured to feed a gaseous C1-containing substrate from the industrial facility to the bioreactor vessel, the inlet gas port extending into the interior of the bioreactor vessel and in fluid communication with a gas distribution device located within the bioreactor, the gas outlet port located proximate to the top end of the vertically extending bioreactor vessel in fluid communication with the bioreactor and configured to withdraw gaseous products, including unreacted C1-containing substrate, from the bioreactor vessel; the bioreactor vessel further comprising a liquid inlet port and a liquid outlet port, the liquid inlet port positioned below the gas inlet port and configured to introduce a culture medium comprising at least one C1-fixing microorganism into the bioreactor vessel, the liquid outlet port positioned below the gas inlet port and configured to withdraw liquid products from the bioreactor vessel; the fermentation unit housed within a container having a volume of less than about 6 $m^3$.

14. The fermentation unit of claim 13, wherein the bioreactor vessel further comprises an external recycle loop and recirculation pump, the recycle loop comprising piping means in fluid communication with the bioreactor vessel through an exit recycle port located proximate to the bottom end of the bioreactor vessel, the piping means being in fluid communication with the recirculating pump configured to pump a fermentation broth from the exit recycle port through said piping means to an inlet recycle port located proximate to the top end of the bioreactor vessel, said inlet recycle port in fluid communication with a liquid distribution device located inside the top end on the bioreactor vessel.

15. The fermentation unit of claim 13, wherein the container has length, width, and height dimensions of less than about 1.8 meters each.

16. The fermentation unit of claim 15, wherein the container has one of the length, width, and height dimensions of less than about 1.6 meters, and the other two of the length, width, and height dimensions of less than about 1.3 meters.

17. The fermentation unit of claim 14, wherein the liquid distribution device is a shower head.

18. The fermentation unit of claim 14, wherein the recycle loop further comprises a basic neutralizing agent inlet port in fluid communication with a basic neutralizing agent source.

19. The fermentation unit of claim 14, further comprising a basic neutralizing inlet port in fluid communication with a basic neutralizing agent source, the port configured to feed the basic neutralizing agent to the bioreactor vessel.

20. The fermentation unit of claim 13, wherein the gas distribution device is a sparger and is located within the bottom 25% of the bioreactor vessel.

\* \* \* \* \*